(12) United States Patent
Fujikawa et al.

(10) Patent No.: US 7,621,899 B2  
(45) Date of Patent: *Nov. 24, 2009

(54) SANITARY NAPKIN

(75) Inventors: Shinobu Fujikawa, Mitoyo-gun (JP); Toshiyuki Tanio, Mitoyo-gun (JP); Wataru Yoshimasa, Mitoyo-gun (JP)

(73) Assignee: Uni-Charm Corporation, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/402,471

(22) Filed: Apr. 11, 2006

(65) Prior Publication Data

US 2006/0282059 A1 Dec. 14, 2006

(30) Foreign Application Priority Data

Jun. 10, 2005 (JP) .............................. 2005-171495

(51) Int. Cl.
 *A61F 13/15* (2006.01)
 *A61F 13/20* (2006.01)
(52) U.S. Cl. .................... 604/385.101; 604/385.17
(58) Field of Classification Search ........... 604/385.01, 604/367, 385.101, 385.17–385.18, 904
 See application file for complete search history.

(56) References Cited

U.S. PATENT DOCUMENTS

| 4,046,147 A | * | 9/1977 | Berg | .................. 604/385.201 |
| 5,853,403 A | * | 12/1998 | Tanzer et al. | ........... 604/385.09 |
| 2006/0142724 A1 | * | 6/2006 | Watanabe et al. | ...... 604/385.04 |

FOREIGN PATENT DOCUMENTS

| EP | 1 097 685 A2 | * | 5/2001 |
| JP | 11-033054 A | | 2/1999 |
| JP | 11-318979 A | | 11/1999 |
| JP | 2000-083993 A | | 3/2000 |
| JP | 2001-504727 A | | 4/2001 |
| JP | 2002-159534 A | | 6/2002 |
| WO | WO-98/22060 A1 | | 5/1998 |

OTHER PUBLICATIONS

Machine Translation of JP 2002-159534; Higuchi Tomoe; Sanitary Aritcle;Jun. 4, 2002.*

* cited by examiner

*Primary Examiner*—Michele Kidwell  
(74) *Attorney, Agent, or Firm*—Darby & Darby P.C.

(57) ABSTRACT

A sanitary napkin includes a main body having a liquid-absorbent layer for absorbing and retaining liquid and a projection disposed on a body surface of the main body. At least a portion of the projection is separably fixed to the body surface of the main body through a temporarily fixing means.

17 Claims, 16 Drawing Sheets

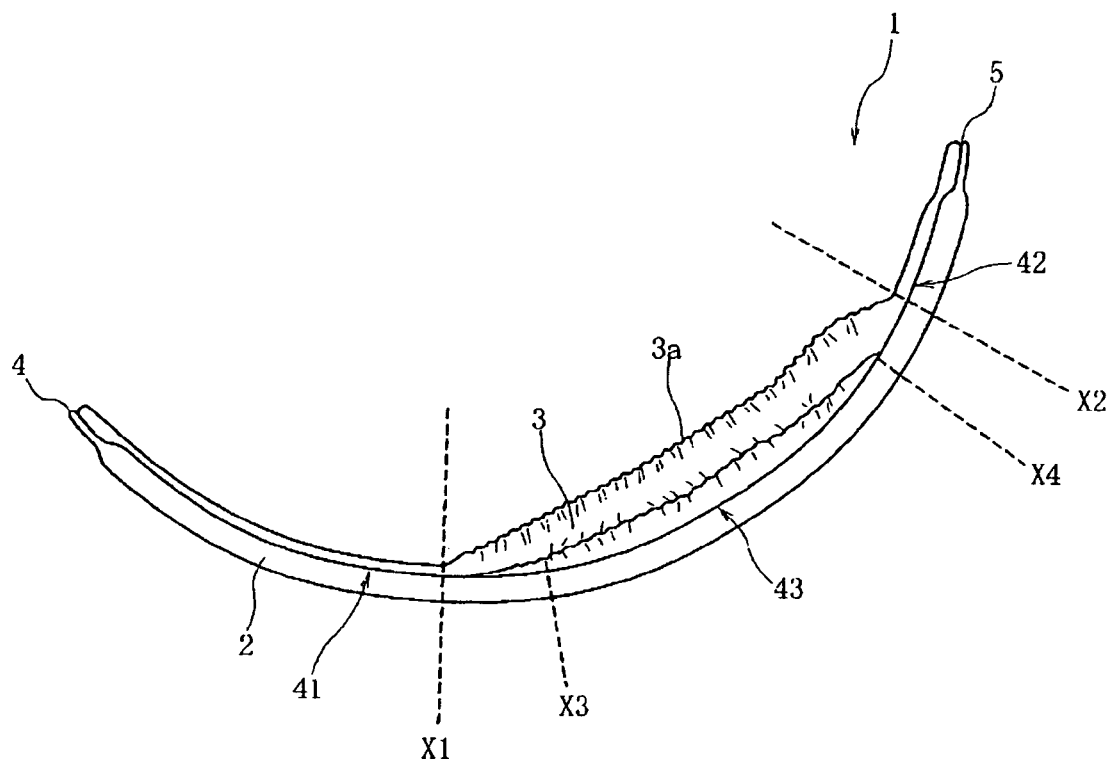
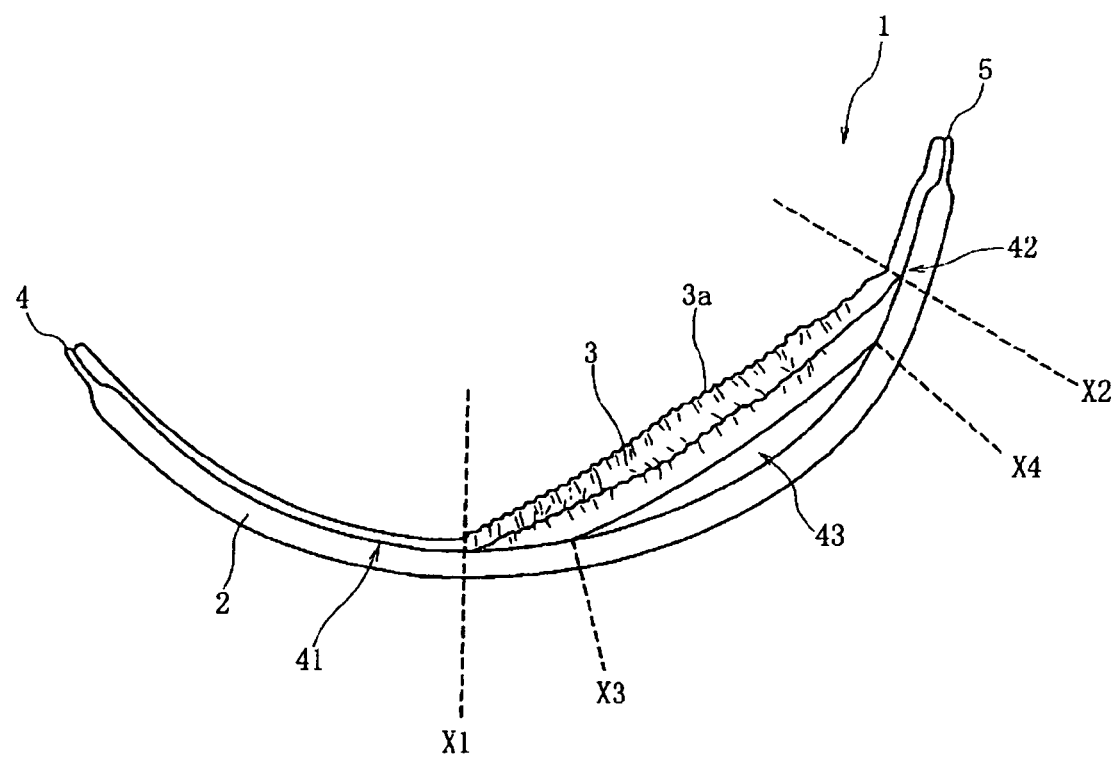

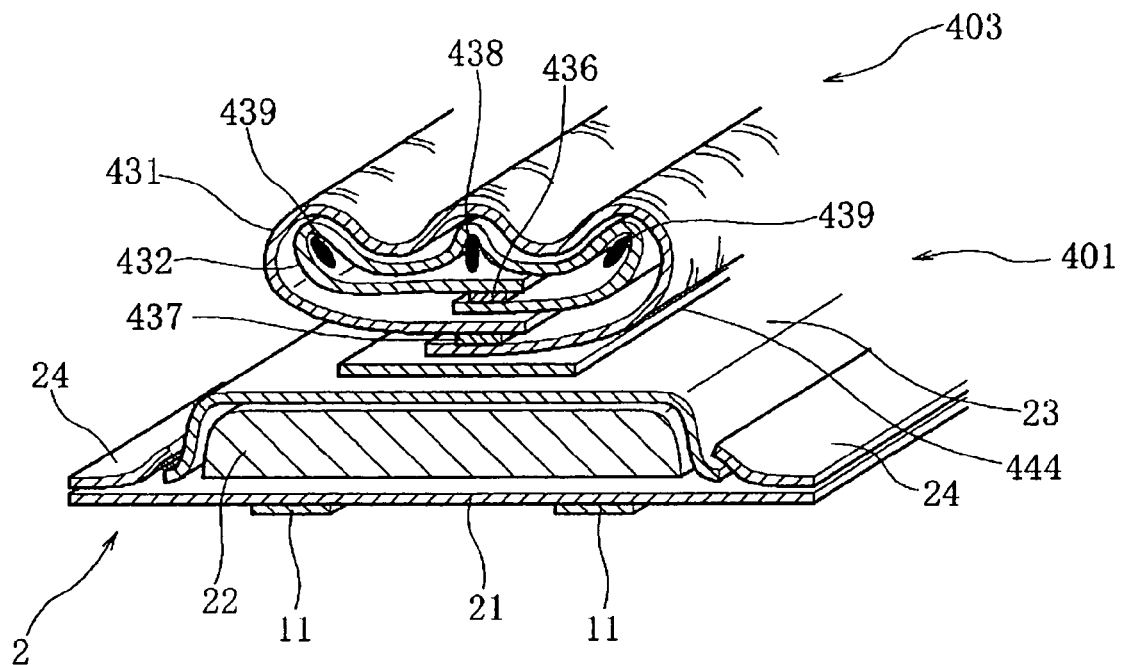
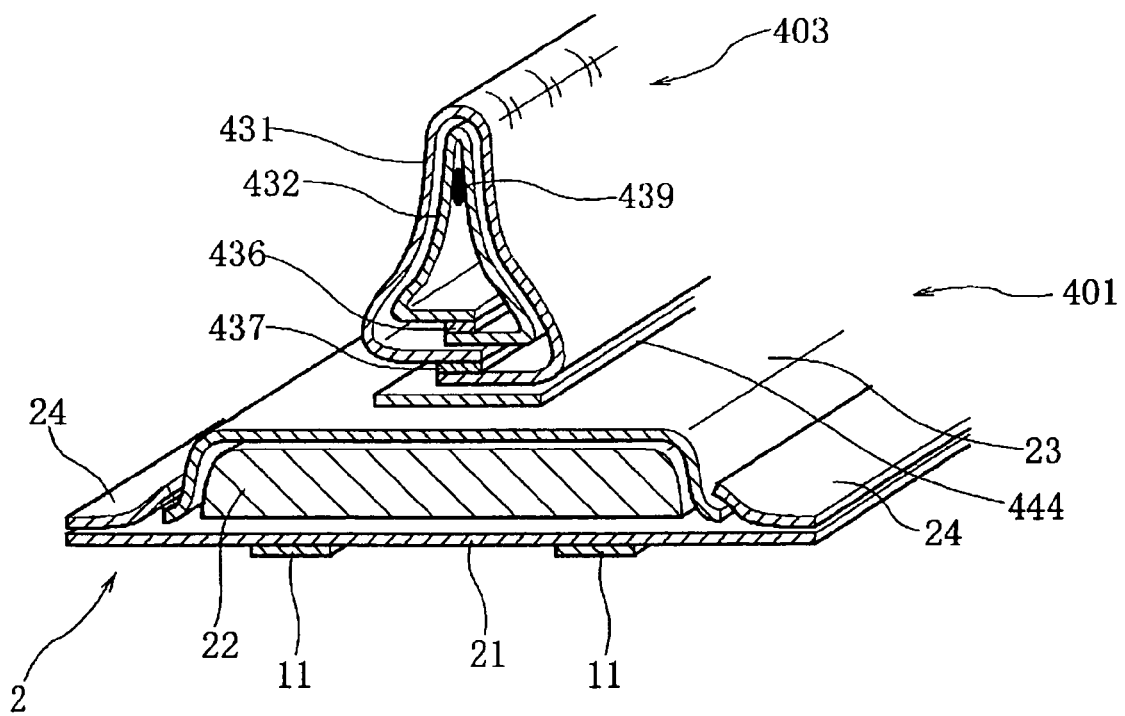

SANITARY NAPKIN

CROSS REFERENCE TO RELATED APPLICATION

This application claims the benefit of priority from Japanese Patent Application No. 2005-171495, filed on Jun. 10, 2005, which is incorporated herein by reference in its entirety.

BACKGROUND OF THE INVENTION

1. Field of the Invention

The present invention relates to a sanitary napkin with a projection on a body surface of a main body, and more particularly to a sanitary napkin whose projection can easily be brought into contact with the a desired region of the wearer's crotch upon wearing and kept in contact with the wearer's crotch even when the main body moves during wear so as to be effective in preventing leakage of menstrual blood.

2. Description of the Related Art

There have been known sanitary napkins of the type including a main body with a liquid-absorbent layer and a projection disposed on the body surface of the main body.

Japanese Unexamined Patent Application Publication No. 2001-504727 discloses a sanitary napkin with a liquid-absorbent layer and a topsheet covering the body surface of the liquid-absorbent layer. Between the topsheet and the liquid-absorbent layer, there is provided a hump to form a projection. This hump has the ability to absorb liquid. The hump is shaped to gradually decrease in width and height toward front and rear ends. This sanitary napkin is aimed at preventing leakage of menstrual blood by keeping the hump in contact with a groove of the wearer's body from the vaginal opening to the intergluteal cleft.

Japanese Unexamined Patent Application Publication No. 2000-83993 discloses a sanitary napkin whose liquid-absorbent layer is composed of separate upper and lower cores. The lower core is integral with a liquid-impermeable lower sheet. On the body surface side of the lower core, there is provided a liquid-permeable upper sheet. Front and rear ends of the upper sheet are secured to the lower core, and elastic members are secured to the upper sheet in order to exert a longitudinal elastic contractive force. The upper core is also secured to the upper sheet. The upper core, as well as the upper sheet, can be raised from the lower core by the elastic contractive force. The upper core can face the wearer's vulva while the outer surface of the lower sheet is attached to the inner side of a crotch part of an undergarment. Japanese Unexamined Patent Application Publication No. H11-318979 discloses a sanitary napkin having a similar structure to that disclosed in JP 2000-83993.

Japanese Unexamined Patent Application Publication No. 2002-159534 discloses a sanitary product in which a narrow absorbent member, which is intended to face both the vaginal opening and the buttocks, is disposed on the body surface of a liquid retaining member with a wide absorbent core. The absorbent member is secured to the liquid retaining member at its front end, but not secured to the liquid retaining member at its rear end. This sanitary product is aimed at improving contact of the absorbent member with the wearer's crotch by adhering the rear end of the absorbent member to the wearer's body while the liquid retaining member is fixed to an inner side of an undergarment.

The sanitary napkin with the projection on the body surface of the main body may be used such that the main body is fixed to an inner side of a crotch part of an undergarment through a pressure-sensitive adhesive layer to bring the projection into contact with the vaginal opening and/or the intergluteal cleft. However, as the wearer's body moves while wearing the sanitary napkin, the undergarment is stretched or moved laterally by the motion of the buttocks. Therefore, the sanitary napkin fixed on the undergarment tends to move laterally following the deformation of the undergarment. For example, as a wearer walks with the sanitary napkin worn in the crotch, the sanitary napkin moves from side to side along with the undergarment.

In the sanitary napkin disclosed in JP 2001-504727, since the hump (or projection) is integrally formed on the body surface of the main body, the projection moves along with the main body and easily separates from the vaginal opening or the intergluteal cleft as the main body adhered to the undergarment moves along with the undergarment, creating a clearance between the wearer's body and the sanitary napkin to cause lateral or rearward leakage of menstrual blood.

In the sanitary napkin disclosed in JP 2000-83993, since the body surface of the upper core, which is to be in contact with vaginal opening, is relatively flat, there is a possibility that as the lower core moves laterally following the motion of the undergarment, the upper core also moves laterally following the motion of the lower core. Upon wearing sanitary napkin, moreover, it is required to adhere the lower core to the inner side of the crotch part of the undergarment and then pulling the sanitary napkin up toward the wearer's crotch along with the undergarment. At this time, since the lower core is concavely curved in the longitudinal direction to conform to the shape of the crotch part of the undergarment, a force to raise the upper core due to the elastic members will decrease, so that the upper core becomes liable to move over the lower core. When the sanitary napkin is pulled up and worn along with the undergarment, therefore, the upper core may be displaced laterally with respect to a target region such as the vaginal opening. This is also true for the sanitary napkin disclosed in JP H11-318979.

In the sanitary product disclosed in JP 2002-159534, only the front end of the narrow absorbent member is fixed to the liquid retaining member to leave the rear portion freely movable. Therefore, when the sanitary product is fixed to the crotch part of the undergarment and applied to the wearer's crotch along with the undergarment, it is difficult to bring the absorbent member, whose rear portion can move freely, into contact with the vaginal opening and the intergluteal cleft without fail.

SUMMARY OF THE INVENTION

The present invention has been developed to solve the problems in the prior art and has an object to provide a sanitary napkin with a projection which can easily be brought into contact with a desired region of the wearer's crotch upon wearing and move independently of a main body to follow the motion of the wearer's body during wear, thereby ensuring contact with the wearer's body so as to be effective in preventing leakage of menstrual blood.

According to the present invention, there is provided a sanitary napkin comprising:

a main body having a liquid-absorbent layer for absorbing and retaining liquid; and a projection disposed on a body surface of the main body, wherein at least a portion of the projection is separably fixed to the body surface of the main body through a temporarily fixing means.

In the sanitary napkin, since the projection and the main body can be kept in a separably fixed state until the sanitary napkin is applied to the wearer's crotch, it is ensured that the projection will come into contact with intergluteal cleft and/ or the vaginal opening. After the sanitary napkin is applied to the wearer's crotch, when the main body moves laterally under the influence of the motion of the wearer's body, the projection fitting in a groove of the wearer's body and the main body are pulled in generally opposite directions. At this time, the projection can be separated from the main body. This keeps the projection in contact with the wearer's body even if the main body moves laterally, thereby preventing leakage of menstrual blood out of the napkin. Alternatively, the projection may be separated from the main body by hands after the sanitary napkin is applied to the wearer's crotch.

In the present invention, another portion of the projection may be firmly fixed to the body surface of the main body through a firmly fixing means which provides a higher bond strength than the temporarily fixing means. In this case, only the separably fixed portion of the projection is allowed to separate from the main body so as to be moveable independently of the main body.

According to one embodiment of the present invention, the projection may have front and rear portions and an intermediate portion located between the front and rear portions, the front and rear portions being firmly fixed to the body surface of the main body through the firmly fixing means, the intermediate portion being separably fixed to the body surface of the main body through the temporarily fixing means. For example, the projection may be configured to face the intergluteal cleft of a wearer at the intermediate portion. Alternatively, the projection may be configured to face the vaginal opening of a wearer at the intermediate portion. If only the intermediate portion of the projection is made separable with the front and rear portions firmly fixed to the main body, when the longitudinal centerline of the main body coincides with the median plane of the wearer's body such as in an upright position, the projection can easily be straightened along the longitudinal centerline of the main body.

According to another embodiment of the present invention, the projection may be divided into front and rear portions, the rear portion being separably fixed to the body surface of the main body through the temporarily fixing means, the front portion being firmly fixed to the body surface of the main body through the firmly fixing means. With this construction, the rear portion of the projection after separation from the main body can move widely to follow the motion of the wearer's body, maintaining contact of the projection with the groove of the wearer's body.

In this construction, the rear portion may have a tab at a rear end thereof so that the projection can easily be separated from the main body by pulling the tab with fingers after the sanitary napkin is worn in the wearer's crotch along with an undergarment. Preferably, the tab is not fixed to the main body.

In the present invention, the projection may include a longitudinally extending connection sheet and an upper structure, the connection sheet being fixed to the body surface of the main body through the temporarily fixing means and firmly fixing means, the upper structure being firmly fixed to a body surface of the connection sheet. With this construction, the manufacturing process can be simplified because the sanitary napkin may be assembled by first fixing the connection sheet to the main body through the temporarily fixing means and firmly fixing means and then fixing the upper structure of the projection to the connection sheet through an adhesive or the like.

According to still another embodiment of the present invention, the whole projection may be separably fixed to the body surface of the main body through the temporarily fixing means.

In the present invention, the temporarily fixing means may be provided by partially pressing a component of the projection against the body surface of the main body. In an alternative, the temporarily fixing means may be provided by partially fusion-bonding a component of the projection to the body surface of the main body. In another alternative, the temporarily fixing means may be an adhesive layer through which the projection is separably bonded to the body surface of the main body.

In still another alternative, the temporarily fixing means may be provided by perforating a component of the projection at intervals. In this case, the projection may be separated partially or wholly from the main body by tearing the component of the projection along perforation.

In the present invention, as has been described hereinabove, since the projection is an integral part of the main body, it is easy to position the projection along a desired region of the wearer's body. In addition, since the projection is movable independently of the main body during wear, the projection can easily be kept in contact with the desired region, eliminating the fear of rearward leakage of menstrual blood.

BRIEF DESCRIPTION OF THE DRAWINGS

The present invention will be understood more fully from the detailed description given hereinafter and from the accompanying drawings of the preferred embodiments of the present invention, which, however, should not be taken to limit the invention, but are for explanation and understanding only.

In the drawings:

FIG. 8(A) is a side view of the sanitary napkin in a state where no external force is exerted thereon, and FIG. 8(B) is a side view of the sanitary napkin in a state where a part of the projection is separated from the main body;

FIG. 20 is a sectional view taken along line XX-XX of FIG. 18;

FIG. 21 is a sectional view taken along line XXI-XXI of FIG. 18; and

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
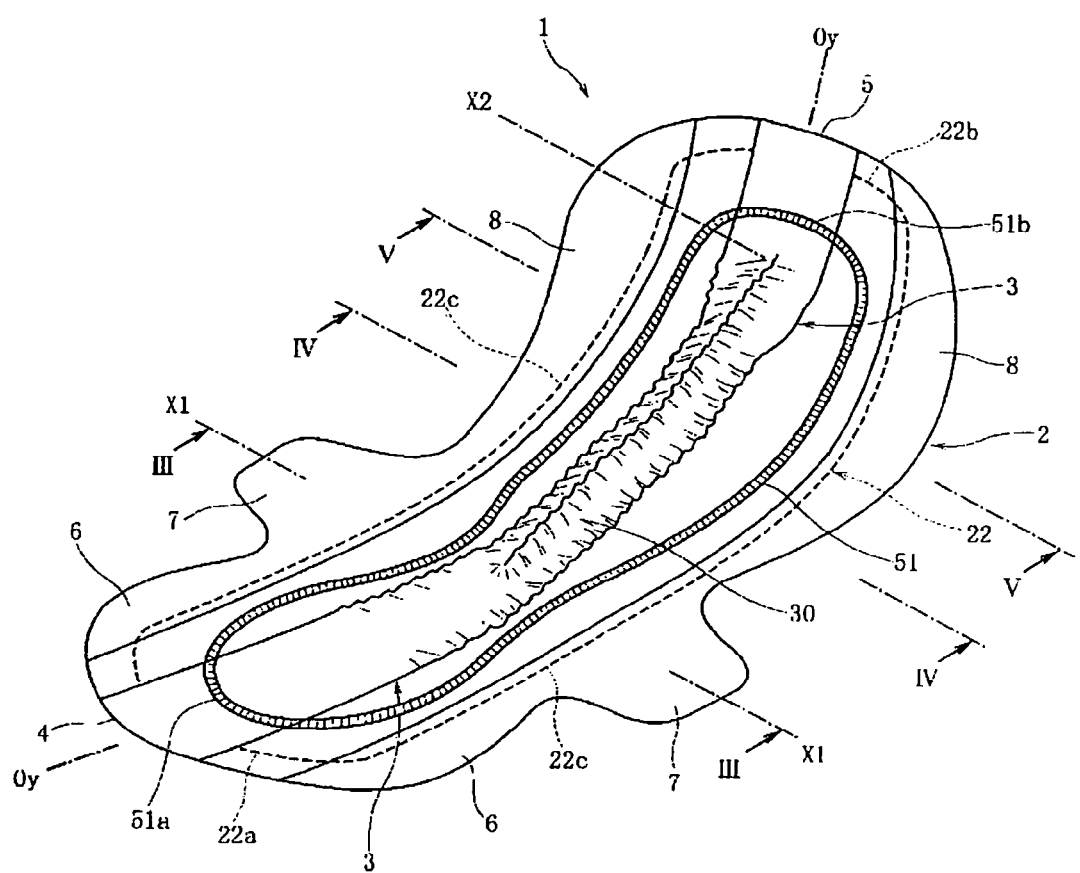
FIG. 1 is a perspective view of a sanitary napkin according to a first embodiment of the present invention in a state where no external force is exerted thereon.
Figure 2:
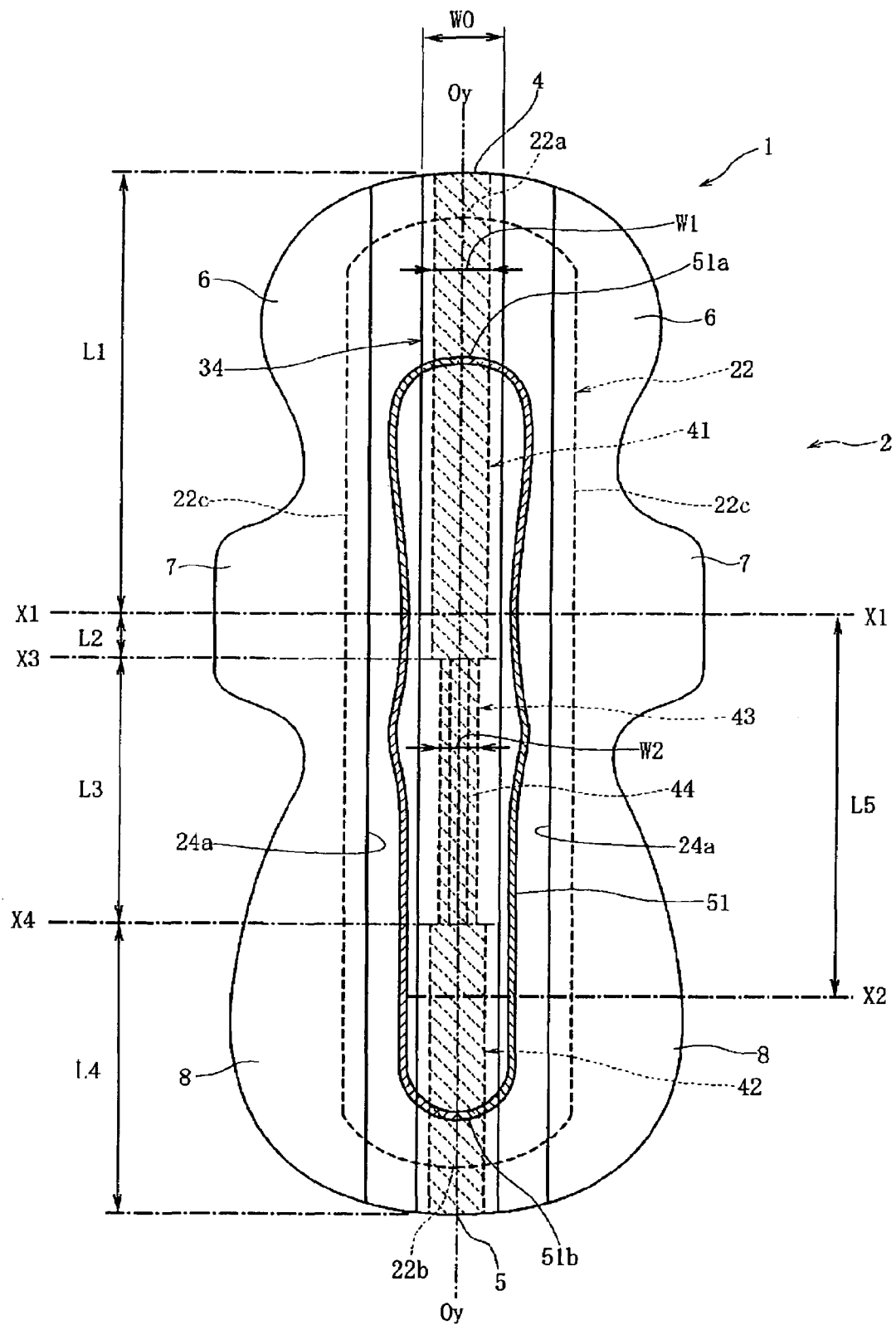
FIG. 2 is a plan view of the sanitary napkin in a flattened state, showing how a connection sheet is fixed to a main body.
Figure 3:
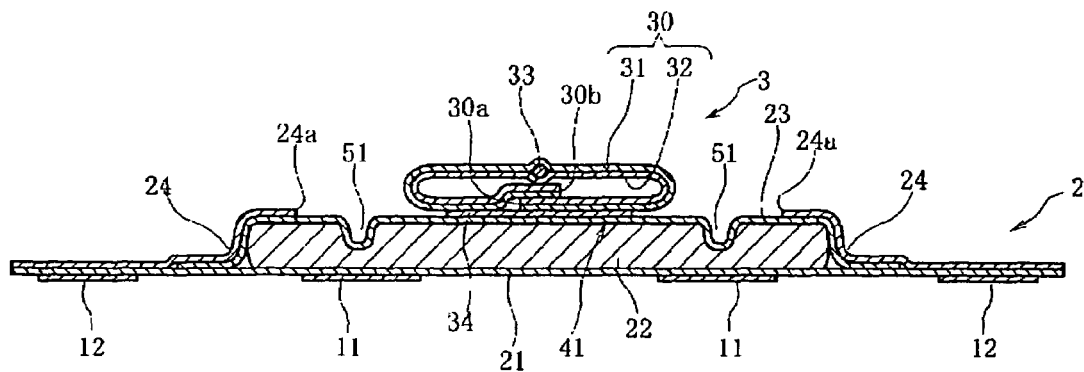
FIG. 3 is a sectional view taken along line III-III of FIG. 1.
Figure 4:
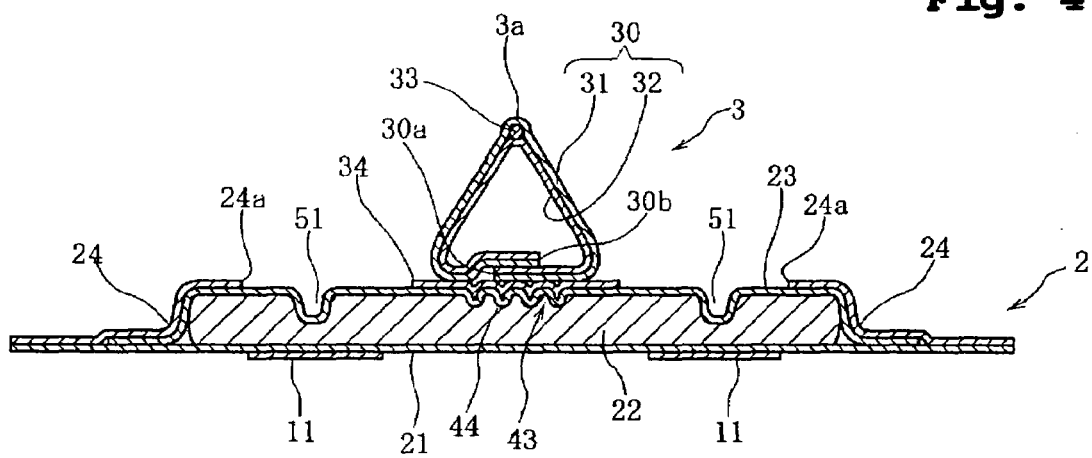
FIG. 4 is a sectional view taken along line IV-IV of FIG. 1.
Figure 5:
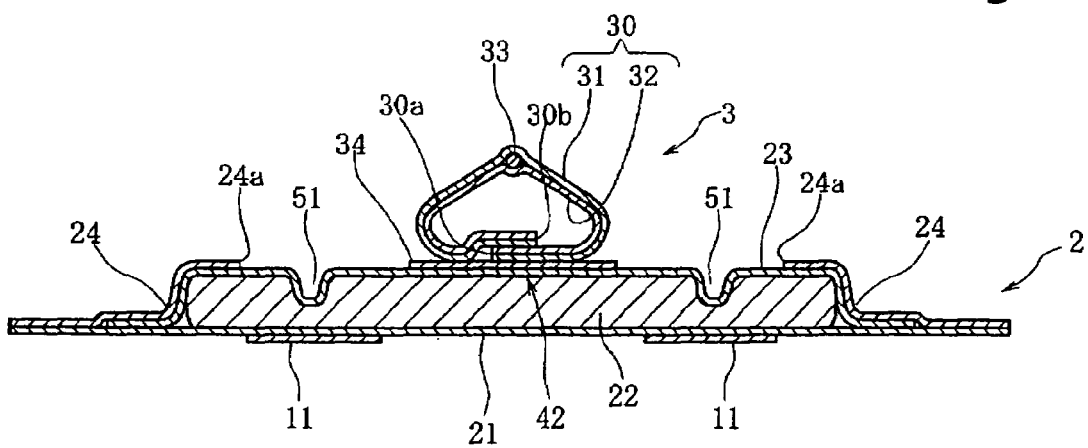
FIG. 5 is a sectional view taken along line V-V of FIG. 1.
Figure 6:
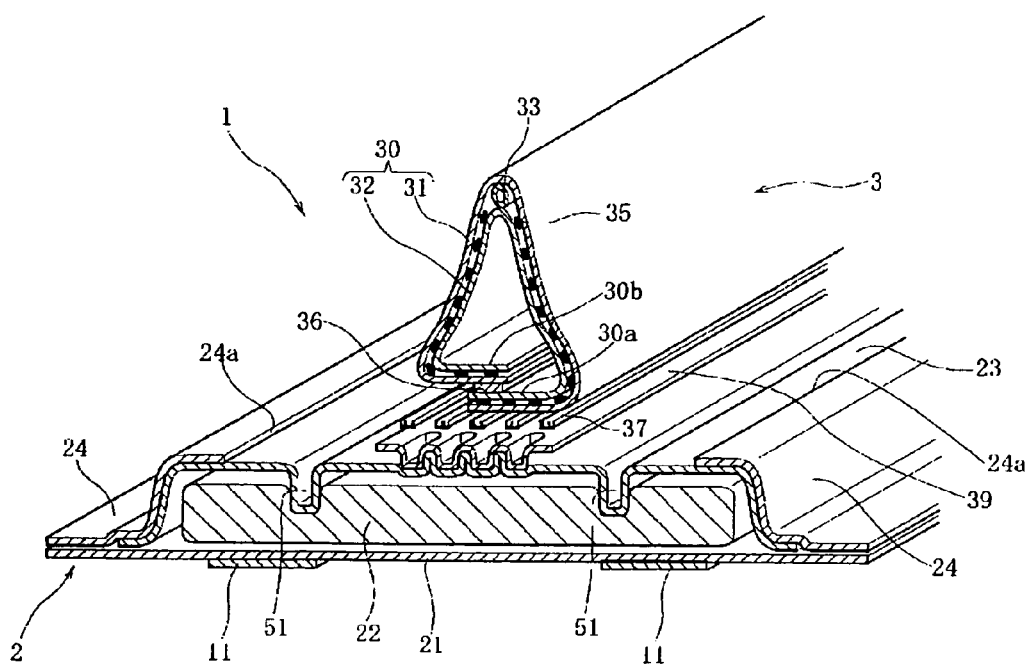
FIG. 6 is a sectioned perspective view for more detailed description of the section of FIG. 4.
Figure 7:
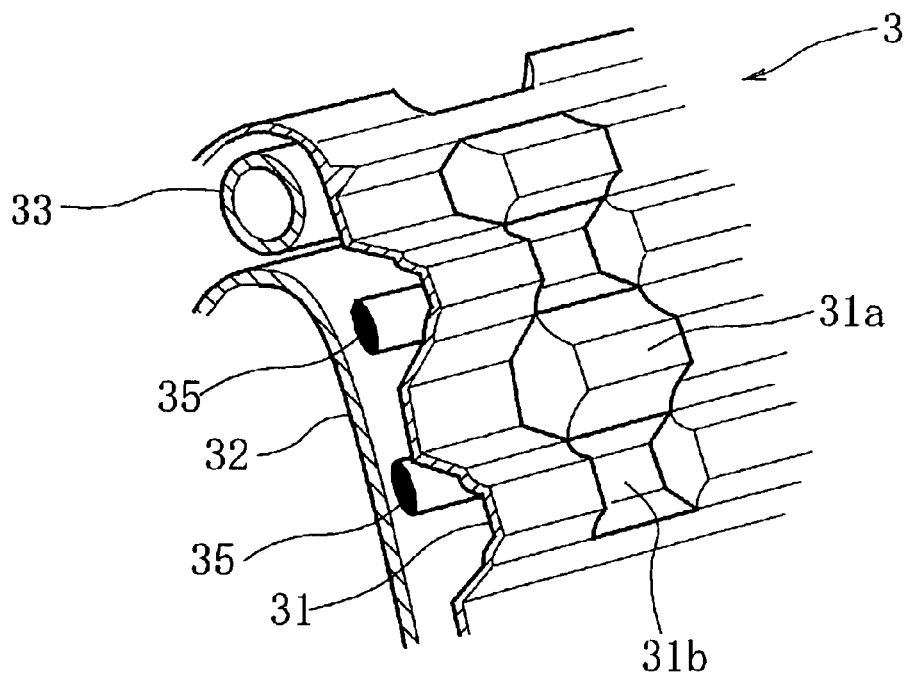
FIG. 7 is an enlarged sectioned perspective view showing a part of a projection on an enlarged scale.
Figure 9A:
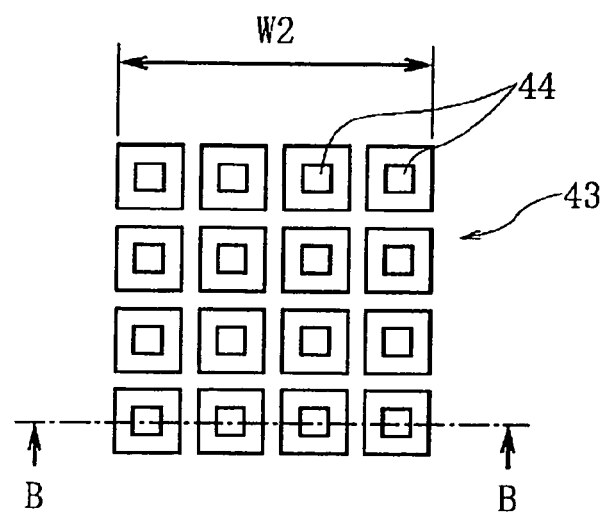
FIG. 9(A) is an enlarged plan view showing embossments being temporarily fixing means.
Figure 9B:
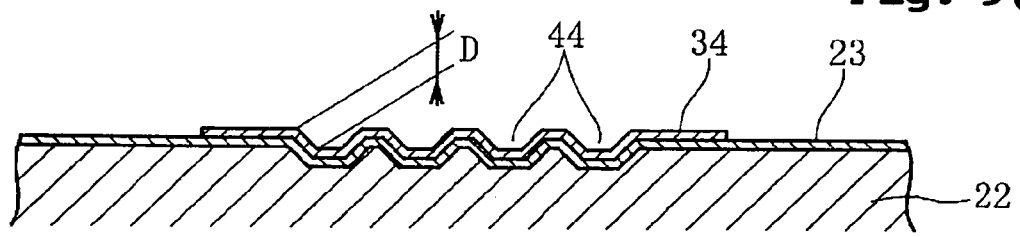
FIG. 9(B) is a sectional view taken along line B-B of FIG. 9(A)

FIG. 1 is a perspective view of a sanitary napkin according to a first embodiment of the present invention in a state where no external force is exerted thereon. FIG. 2 is a plan view of the sanitary napkin in a flattened state, showing how a connection sheet is fixed to a main body. FIG. 3 is a sectional view taken along line III-III of FIG. 1, FIG. 4 is a sectional view taken along line IV-IV of FIG. 1, and FIG. 5 is a sectional view taken along line V-V of FIG. 1. FIG. 6 is a sectioned perspective view for more detailed description of the section taken along the line IV-IV of FIG. 1. FIG. 7 is an enlarged sectioned perspective view showing a part of a projection on an enlarged scale. FIG. 8(A) is a side view of the sanitary napkin in a state where no external force is exerted thereon, and FIG. 8(B) is a side view of the sanitary napkin in a state where a part of the projection is separated from the main body. FIG. 9(A) is an enlarged plan view showing means for temporarily fixing the connection sheet to the main body, and FIG. 9(B) is a sectional view taken along line B-B of FIG. 9(A).

It should be noted that the sanitary napkin, as well as its individual components, has two major surfaces: of which one surface intended to be worn toward the wearer's crotch is referred to as "body surface", while the other surface is referred to as "garment surface". In addition, the lengthwise direction of the sanitary napkin is referred to as "longitudinal direction", while the direction perpendicular to the longitudinal direction is referred to as "lateral direction". With respect to dimensions of the individual components, unless otherwise stated, a dimension measured in the longitudinal direction is referred to as "length", while a dimension measured in the lateral direction is referred to as "width".

In the following embodiments, the sanitary napkin includes a main body mainly constituted of a liquid-absorbent layer and a backsheet and a projection bulging from the body surface of the main body. The sanitary napkin further includes a topsheet which may be adopted only for the main body or for both the main body and the projection.

The projection is fixed to the main body through a temporarily fixing means or a firmly fixing means. The temporarily fixing means may be providing by pressing, fusion-bonding, applying an adhesive layer, etc. The projection, which is fixed through the temporarily fixing means, can easily be separated from the main body by hands without causing severe damage to components of the projection and the main body. That is, the temporarily fixing means provides such a bond strength as to ensure that the projection and the main body will be separated from each other without changing in shape. The firmly fixing means provides a higher bond strength than the temporarily fixing means. In other words, the firmly fixing means requires a larger force to separate the projection from the main body than the temporarily fixing means. Separation of the projection and the main body, which are fixed together through the firmly fixing means, causes severe damage to a component of at least one of the projection and the main body, so that at least one of the projection and the main body will loose its original shape.

According to the first embodiment, a sanitary napkin 1 includes a main body 2 and a projection 3 disposed on the body surface of the main body 2.

As shown in FIGS. 3 to 5, the main body 2 includes a liquid-blocking backsheet 21 lying on the garment surface side of the main body 2, a liquid-absorbent layer 22 disposed on the backsheet 21, a liquid-permeable topsheet 23 covering the liquid-absorbent layer 22, and side sheets 24, 24 lying on the body surface side of the main body 2 and opposite one another in the lateral direction. These components are bonded together through a hot-melt type adhesive.

As shown in FIGS. 1 and 2, the main body 2 has arcuate front and rear edges 4, 5. The main body 2 is elongated to have a length of 280 to 450 mm on a longitudinal centerline Oy. In the first embodiment, the length of the main body 2 is, for example, 350 mm. The liquid-absorbent layer 22 is also elongated to have arcuate front and rear edges 22a, 22b, which are spaced slightly inward from the front and rear edges 4, 5, respectively. The liquid-absorbent layer 22 has right and left side edges 22c, 22c, which extend linearly in parallel to the longitudinal centerline Oy. However, the shape of the right and left side edges 22c, 22c of the liquid-absorbent layer 22 should not be understood as limited to this embodiment.

Outside the side edges 22c, 22c of the liquid-absorbent layer 22, the main body 2 has laterally projecting front flaps 6, 6, laterally projecting fold-back flaps 7, 7, and laterally projecting rear flaps 8, 8 in order from front to rear. In the front flaps 6, 6, the fold-back flaps 7, 7, and the rear flaps 8, 8, the side sheets 24 are laid on and bonded to the backsheet 21 through a hot-melt type adhesive.

The side sheets 24, 24 lie opposite one another in the lateral direction with their opposing edges 24a, 24a located inside the side edges 22c, 22c of the liquid-absorbent layer 22 (i.e., located closer to the longitudinal centerline Oy than the side edges 22c, 22c). At the laterally opposite side portions of the liquid-absorbent layer 22, as shown in FIGS. 3 to 5, the body surface of the liquid-absorbent layer 22 is covered with the topsheet 23, and the body surface of the topsheet 23 is further covered with the side sheets 24, 24. In the area defined between the opposing edges 24a, 24a of the side sheets 24, 24, the liquid-permeable topsheet 23 is exposed externally. The overlap between this area and the liquid-absorbent layer 22 is called "main liquid-absorbent region".

X1 shown in FIGS. 1 and 2 represents a vagina-facing reference line, and FIG. 3 is a sectional view of the sanitary napkin 1 taken along the vagina-facing reference line X1. The vagina-facing reference line X1 is spaced a distance L1 of 100 to 200 mm, preferably 100 to 140 mm, rearward from the front edge 4 of the main body 2. In the first embodiment, for example, the distance L1 is about 120 mm.

The intersection of the vagina-facing reference line X1 and the longitudinal centerline Oy is called "vagina-facing reference position". The vagina-facing reference position is a target position with which the center of the vaginal opening is to almost coincide when wearing the sanitary napkin 1 along with an undergarment. Leading to this target is through the contour of the sanitary napkin as viewed from the body surface side or the whole design including the arrangement of compression line 51 on the body surface. Particularly when the fold-back flaps 7, 7 are provided as in the present embodiment, the vagina-facing reference line X1 usually coincides with the longitudinal centers of the fold-back flaps 7, 7. Also in the present embodiment, the lateral distance between right and left side portions of the compression line 51 is reduced on the vagina-facing reference line X1 to facilitate positioning of the sanitary napkin 1.

As shown in FIGS. 3 to 5, the projection 3 has an upper structure and a lower structure. The upper structure is composed of a laminated sheet 30 (being a laminate of an exterior sheet 31 and an interior sheet 32) and an elastic member 33 disposed between the exterior sheet 31 and the interior sheet 32. The lower structure is a connection sheet 34 disposed between the laminated sheet 30 and the topsheet 23 of the main body 2. In short, the projection 3 of the first embodiment is composed of the laminated sheet 30, the elastic member 33 and the connection sheet 34. The exterior sheet 31, the interior sheet 32 and the connection sheet 34 are made of hydrophilic and liquid-permeable materials.

As shown in FIG. 2, the connection sheet 34 is a strip having a uniform width W0. The width W0 of the connection sheet 34 may be in the range of about 10 to 30 mm. In this embodiment, for example, the width W0 is 18 mm. The connection sheet 34, whose longitudinal centerline coincides with the longitudinal centerline Oy of the sanitary napkin 1, extends continuously from the front edge 4 to the rear edge 5 of the sanitary napkin 1.

In front and rear firmly fixing regions 41, 42 shown in FIG. 2, the connection sheet 34 and the topsheet 23 of the main body 2 are firmly fixed together through a firmly fixing means. In a temporarily fixing region 43 located between the front and rear firmly fixing regions 41, 42, on the other hand, the connection sheet 34 and the topsheet 23 are separably fixed together through a temporarily fixing means.

The front firmly fixing region 41 has a length L1+L2, wherein L2 represents a distance measured rearward from the vagina-facing reference line X1. In this embodiment, for example, L2 is 20 mm. X3 represents a boundary between the front firmly fixing region 41 and the temporarily fixing region 43. The temporarily fixing region 43 extends over a length L3 rearward from the boundary X3. In this embodiment, for example, the length L2 is about 100 mm. X4 represents a boundary between the rear firmly fixing region 42 and the temporarily fixing region 43. The rear firmly fixing region 42 extends rearward from the boundary X4 to the rear edge 5 of the sanitary napkin 1. When the length of the sanitary napkin 1 is 350 mm on the longitudinal centerline Oy, the rear firmly fixing region 42 may have a length L4 of 110 mm.

In the front and rear firmly fixing regions 41, 42, the connection sheet 34 and the topsheet 23 are bonded together through a hot-melt type adhesive that is applied in such an amount as not to interfere with passage of liquid. In both the regions, the hot-melt type adhesive is applied over a width W1, for example, in a stripe pattern of 2 mm width longitudinal continuous lines which are spaced 2 mm apart from each other in the lateral direction. For example, the width W1 may be in the range of 10 to 18 mm, and the adhesive may be applied in an amount of about 10 g/m$^2$ in the front and rear firmly fixing regions 41, 42. In the front and rear firmly fixing regions 41, 42, alternatively, the topsheet 23 and the connection sheet 34 may be fusion-bonded together such as by heat sealing or ultrasonic sealing.

In the temporarily fixing region 43, as shown in FIGS. 9(A) and 9(B), the connection sheet 34 and the topsheet 23 are separably fixed together by embossments 44, which are provided as the temporarily fixing means. The embossments 44 may be formed by partially pressing the connection sheet 34 and the topsheet 23 at room temperature. The temporarily fixing region 43 has a width W2 which is smaller than the width W1 of the front and rear firmly fixing regions 41, 42. For example, the width W2 is about 8 mm. As shown in FIG. 9(A), the embossments 44 are arranged in four rows parallel to the longitudinal direction. The embossments 44 are equally spaced apart in both the longitudinal and lateral directions. Each embossment 44 is a square whose side is 2 mm or slightly less.

The embossments 44 may be formed by pressing a stack of the connection sheet 34 and the topsheet 23 at room temperature between a flat pressing die or pressing roll with a plurality of protuberances and a flat pressing die or pressing roll with a plurality of recesses that are intended to face the protuberances. At this time, a pressing force is preferably about 200 to 300 N for the whole area of the temporarily fixing region 43 having the width W2 and the length L3. In addition, upon pressing the stack between the pressing dies or pressing rolls, a pressing depth D (see FIG. 9(B)) in a direction from the connection sheet 34 to the topsheet 23 is preferably about 0.2 to 0.8 mm.

In the laminated sheet 30, as shown in FIG. 6 in detail, the exterior sheet 31 and the interior sheet 32 are bonded together through a hot-melt type adhesive 35. The hot-melt type adhesive 35 is applied in a stripe or spiral pattern in such an amount as not to interfere with passage of liquid, for example, in an amount of 2 g/m$^2$. The elastic member 33 is an elastically stretchable filament. The elastic member 33 is bonded to the exterior and interior sheets 31, 32 through a hot-melt type adhesive while being stretched at least 1.2 times the original length.

The laminated sheet 30 is a strip having a uniform width. The laminated sheet 30 is formed into a hollow tube with one edge 30a laid beneath and bonded to the other edge 30b through a hot-melt type adhesive 36, as shown in FIG. 6. The hot-melt type adhesive 36 may be applied in a longitudinal continuous line with a width of about 3 mm in an amount of about 10 g/m$^2$.

As shown in FIG. 1, the tubular laminated sheet 30, whose longitudinal centerline coincides with the longitudinal centerline Oy of the sanitary napkin 1, extends continuously from the front edge 4 to the rear edge 5 of the sanitary napkin 1. As shown in FIG. 6, the bottom portion of the tubular laminated sheet 30 is bonded to the body surface of the connection sheet 34 through a hot-melt type adhesive 37 over the entire length of the connection sheet 34. The hot-melt type adhesive 37 is applied in the same pattern and amount as the hot-melt type adhesive applied between the connection sheet 34 and the topsheet 23 in the front and rear firmly fixing regions 41, 42. That is, over the entire length (i.e., all over the front and rear firmly fixing regions 41, 42 and the temporarily fixing region 43), the laminated sheet 30 and the connection sheet 34 are fixed together to provide the same bond strength as the topsheet 23 and the connection sheet 34 in the front and rear firmly fixing regions 41, 42.

In a process of manufacturing the sanitary napkin 1, at first, the topsheet 23 and the connection sheet 34 are firmly or separably fixed together in the front and rear firmly fixing regions 41, 42 and the temporarily fixing region 43. Then, the backsheet 21, the liquid-absorbent layer 22 and the topsheet 23 with the connection sheet 34 are stacked to form the main body 2. Thereafter, the laminated sheet 30 is fixed to the body surface of the connection sheet 34 through the hot-melt type adhesive 37. The sanitary napkin 1 with the front and rear firmly fixing regions 41, 42 and the temporarily fixing region 43 can easily be manufactured by bonding the connection sheet 34 and the laminated sheet 30 after bonding the connection sheet 34 and the topsheet 23.

The front end of the elastic member 33 is located in front of the vagina-facing reference line X1. In the area between the vagina-facing reference line X1 and the front edge 4, the laminated sheet 30 is folded flat, as shown in FIG. 3. More specifically, vertically opposite inner surfaces of the laminated sheet 30 are bonded together at least in an area where the elastic member 33 is present, thereby securing the elastic member 33 on the body surface of the main body 2. On the other hand, the rear end of the elastic member 33 is located behind a rear reference line X2. The rear reference line X2 is located slightly in front of a rear end portion 51b of the compression line 51. Also in the area between the rear reference line X2 and the rear edge 5 of the sanitary napkin 1, the laminated sheet 30 is folded flat with vertically opposite inner surfaces being bonded together at least in an area where the elastic member 33 is present, as in FIG. 3. When the laminated sheet 30 is folded flat as shown in FIG. 3, the projection 3 may have a width in the range of 20 to 40 mm. In this embodiment, for example, the projection 3 has a width of 24 mm. Within the above range, the flattened projection 3 can reliably face the vaginal opening.

In the area between the vagina-facing reference line X1 and the rear reference line X2, the tubular laminated sheet 30 remains hollow because the inner surfaces are not bonded together. When no external force is exerted on the sanitary napkin 1, the elastic contractive force exerted by the elastic member 33 acts on the main body 2 to bring the vagina-facing reference line X1 and the rear reference line X2 closer to each other, thereby causing longitudinal curvature of the main body 2 with its body surface recessed as shown in FIG. 8(A). Accordingly, the elastic member 33 moves away from the body surface of the main body 2 to raise the tubular laminated sheet 30 from the body surface of the main body 2.

In front of the vagina-facing reference line X1 and behind the rear reference line X2, therefore, the projection 3 has a small height from the body surface of the main body 2, as shown in FIG. 3; between the vagina-facing reference line X1 and the rear reference line X2, on the other hand, the projection 3 has a large height from the body surface of the main body 2. When the main body 2 is flattened as shown in FIG. 2, the vagina-facing reference line X1 and the rear reference line X2 are spaced a distance L5 of about 140 mm. When no external force is exerted on the sanitary napkin 1, the rising height of the projection 3 measured from the body surface of the main body 2 is increased to a maximum at a midpoint of the area subjected to the elastic contractive force, i.e., at a midpoint between the vagina-facing reference line X1 and the rear reference line X2.

The rising height of the projection 3 is increased to a maximum at a location spaced about 70 mm rearward from the vagina-facing reference line X1, where the projection 3 is intended to face the intergluteal cleft of the wearer's body, preferably the deepest part of the intergluteal cleft. In order that the projection 3 may fit in the intergluteal cleft without giving any unpleasant feeling, the maximum rising height is in the range of 11 to 60 mm, preferably in the range of 15 to 40 mm. At this location where the rising height is increased to a maximum, the projection 3 has a width of about 10 to 30 mm, and more specifically, the distance between the opposite side walls of the laminated sheet 30 gradually increases from an apex 3a containing the elastic member 33 to the main body 2, as shown in FIG. 4.

Also in front of and behind the location where the rising height is increased to a maximum, the distance between the opposite side walls of the projection 3 gradually increases toward the main body 2, as shown in FIG. 5. The opening angle of the opposite side walls about the apex 3a is smallest at the location where the rising height is increased to a maximum.

The exterior sheet 31, which shows on the exterior surface of the projection 3, is formed with fine irregularities, as shown in FIG. 7. The irregularities may be formed by embossing the exterior sheet 31 under heat. In the embodiment shown in FIG. 7, protrusions 31a where the exterior sheet 31 protrudes away from the interior sheet 32 and recesses 31b where the exterior sheet 31 is recessed toward the interior sheet 32 alternate with each other in both the longitudinal and lateral directions. The protrusions 31a are arranged at a pitch of about 0.5 to 3 mm in both the longitudinal and lateral directions. The irregularities formed in the exterior sheet 31 function as means for increasing friction against the wearer's skin. Accordingly, when the projection 3 fits in the intergluteal cleft, the irregularities increase the friction of the surface of the projection 3 against the wearer's skin in the intergluteal cleft, thereby improving contact of the projection 3 with the intergluteal cleft to prevent the projection 3 from slipping off the intergluteal cleft.

As shown in FIGS. 1 and 2, the body surface of the sanitary napkin 1 has the compression line 51 which is formed by pressing and heating the topsheet 23 and the liquid-absorbent layer 22 together. In the front and rear areas of the sanitary napkin 1, front and rear end portions 51a, 51b of the compression line 51 extend across the projection 3. In these overlaps, the laminated sheet 30 of the projection 3 is pressed together with the topsheet 23 and liquid-absorbent layer 22 of the main body 2.

The compression line 51 is formed to enclose an elongated area where the liquid-absorbent layer 22 is present. The compression line 51 increases the stiffness of the main body 2, inhibiting the occurrence of folds in the main body 2 subjected to the elastic contractive force of the elastic member 33. This enables longitudinal uniform curvature of the main body 2.

As shown in FIGS. 3 and 5, the main body 2 has pressure-sensitive adhesive layers 11 on the garment surface of the backsheet 21 for securement to an undergarment. The pressure-sensitive adhesive layers 11 extend in the form of strips on both sides of and in parallel to the longitudinal centerline Oy. For the fold-back flaps 7, 7, the main body 2 also has pressure-sensitive adhesive layers 12 on the garment surface of the backsheet 21, as shown in FIG. 3.

Now there will be described preferred materials for the sanitary napkin 1 according to the first embodiment of the present invention.

The backsheet 21 of the main body 2 may be a polyethylene film having a basis weight of 23.5 g/m². The liquid-absorbent layer 22 may be a mixture of softwood kraft pulp and super-absorbent polymer wrapped in a hydrophilic tissue. The superabsorbent polymer content may be about 3% by weight of the liquid-absorbent layer 22. The basis weight of the liquid-absorbent layer 22 may be about 400 g/m². The topsheet 23 of the main body 2 may be a hydrophilic and liquid-permeable nonwoven fabric or a resin film with a large number of apertures for passage of liquid. For example, the topsheet 23 may be a through-air bonded nonwoven fabric formed by bonding synthetic resin fibers through a hot air, wherein the synthetic resin fibers may be 2.2 dtex sheath/core bicomponent fibers of which the core is polyester and the sheath is polyethylene. The topsheet 23 may have a basis weight of about 25 g/m². The side sheet 24 may be a 22 g/m² spunbonded nonwoven fabric of 2.2 dtex sheath/core bicomponent fibers of which the core is polypropylene and the sheath is polyethylene.

The connection sheet 34 may be a hydrophilic and liquid-permeable nonwoven fabric or a synthetic resin film with a large number of apertures for passage of liquid. For example, the connection sheet 34 may be a 22 g/m² spunbonded nonwoven fabric of 2.2 dtex sheath/core bicomponent fibers of which the core is polypropylene and the sheath is polyethylene. Alternatively, the connection sheet 34 may be a through-air bonded or spunlaced nonwoven fabric.

The exterior sheet 31 and the interior sheet 32 of the laminated sheet 30 may be a hydrophilic and liquid-permeable nonwoven fabric or a resin film with a large number of apertures for passage of liquid. For example, the exterior sheet 31 and the interior sheet 32 may be a 25 g/m² through-air bonded nonwoven fabric of 2.2 dtex sheath/core bicomponent fibers of which the core is polyester and the sheath is polyethylene. The elastic member 33 may be a polyurethane elastic filament having a fineness of 1880 dtex.

Now there will be described how the sanitary napkin 1 can behave during use.

In the sanitary napkin 1 before use, the projection 3 is fixed on the main body 2 to function as an integral part in both the front and rear firmly fixing regions 41, 42 and the temporarily fixing region 43. The sanitary napkin 1 is secured to an inner side of a crotch part of an undergarment through the pressure-sensitive adhesive layers 11 disposed on the garment surface of the backsheet 21. At this time, the sanitary napkin 1 is positioned on and adhered to the inner side of the crotch part of the undergarment such that the vagina-facing reference position (which is the intersection of the imaginary vagina-facing reference line X1 and the longitudinal centerline Oy) coincides with the center of the vaginal opening. Furthermore, the fold-back flaps 7, 7 are folded back against an outer side of the undergarment along side edges of the crotch part, thereby securing the garment surface of the fold-back flaps 7, 7 to the outer side of the crotch part of the undergarment through the pressure-sensitive adhesive layers 12.

Before application to the wearer's body, the main body 2 of the sanitary napkin 1 is concavely curved between the vagina-facing reference line X1 and the rear reference line X2 to thereby raise the apex 3a of the projection 3 from the body surface of the main body 2, as shown in FIG. 8(A).

The sanitary napkin 1 can be applied to the woman's crotch by pulling up the undergarment. At this time, since the projection 3 is secured on the main body 2 as an integral part, the raised portion of the projection 3 between the vagina-facing reference line X1 and the rear reference line X2 can easily be positioned along the perineum, the anus and the intergluteal cleft. On or near the vagina-facing reference line X1, the projection 3, which is almost flattened to have a small height as shown in FIG. 3, can be brought into contact with the vaginal opening without giving an unpleasant feeling. Between the vagina-facing reference line X1 and the rear reference line X2, on the other hand, the projection 3, which is raised high and shaped to gradually decrease in width toward the apex 3a as shown in FIGS. 4 and 5, can smoothly fit in the intergluteal cleft. At the midpoint between the vagina-facing reference line X1 and the rear reference line X2 where the rising height of the projection 3 is increased to a maximum, furthermore, the projection 3 fits in the deepest part of the intergluteal cleft. Since the exterior sheet 31 showing on the exterior surface of the projection 3 is formed with the fine irregularities as shown in FIG. 7, the friction of the exterior surface of the projection 3 against the wearer's skin is increased to prevent the projection 3 from easily slipping off the intergluteal cleft.

Figure 11A:
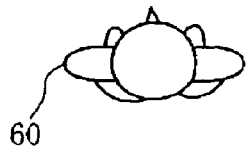
FIGS. 11(A), 11(B), 11(C), 11(D), 11(E) and 11(F) are illustrations showing relationship between motions of the wearer's body and the sanitary napkin's behaviors.
Figure 11B:
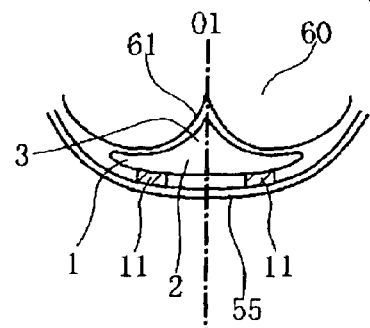
Figure 11C:
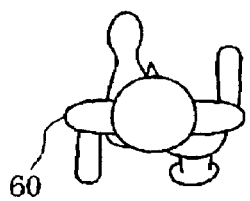
Figure 11D:
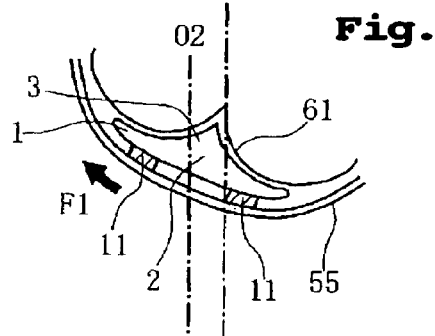
Figure 11E:
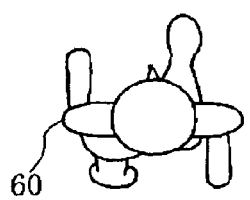
Figure 11F:
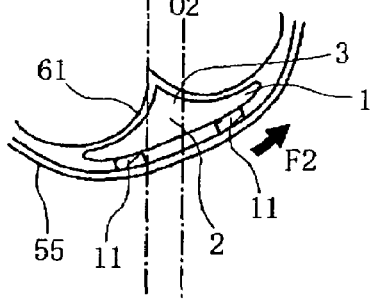

FIGS. 11(A), 11(C) and 11(E) are illustrations where motions of a body 60 wearing the sanitary napkin 1 are viewed from above; and FIGS. 11(B), 11(D) and 11(F) are illustrations showing how the sanitary napkin 1 secured to an undergarment 55 through the pressure-sensitive adhesive layers 11 moves with respect to an intergluteal cleft 61 of the body 60. FIGS. 11(A) and 11(B) show a state where the body 60 is in an upright position; FIGS. 11(C) and 11(D) show a state where the left foot is advanced during walking; and FIGS. 11(E) and 11(F) show a state where the right foot is advanced during walking.

In the upright position, as shown in FIGS. 11(A) and 11(B), the lateral center O2 of the sanitary napkin 1 coincides with the center O1 of the body 60. When the left foot is advanced during walking, as shown in FIGS. 11(C) and 11(D), a leftward force F1 acts on the undergarment 55, so that the main body 2 of the sanitary napkin 1 adhered to the undergarment 55 is drawn leftward as well. When the right foot is advanced during walking, as shown in FIGS. 11(E) and 11(F), a rightward force F2 acts on the undergarment 55, so that the main body 2 is drawn rightward as well.

Figure 12:
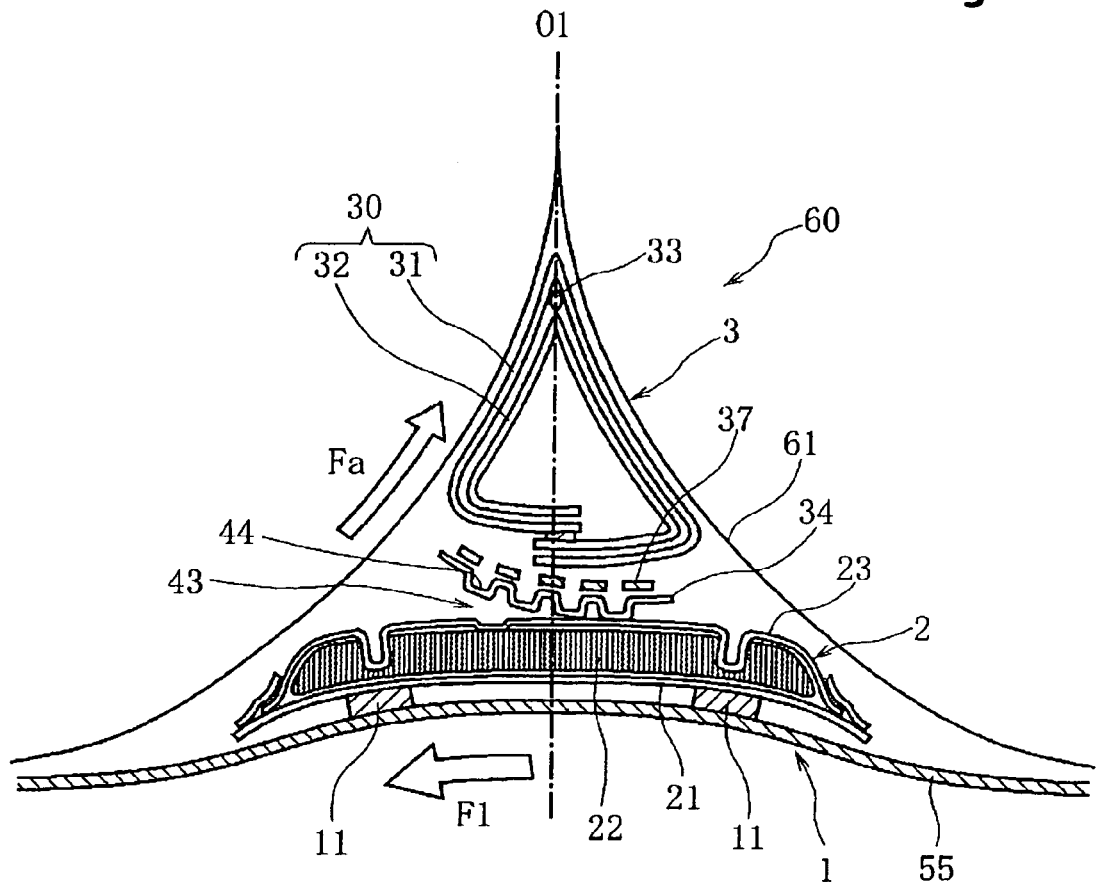
FIG. 12 is an enlarged sectional view showing separation of the projection fitting in the intergluteal cleft from the main body of the sanitary napkin.

As set forth above, the raised portion of the projection 3 between the vagina-facing reference line X1 and the rear reference line X2 fits in the intergluteal cleft. Accordingly, when the main body 2 moves from side to side during walking, the raised portion of the projection 3 fitting in the intergluteal cleft and the main body 2 are subjected to opposite forces. FIG. 12 shows the state of FIG. 11(D) on an enlarged scale. As the force F1 acting on the main body 2 increases, the bonds between the connection sheet 34 and the topsheet 23 due to the embossments 44 are dissolved in the temporarily fixing region 43 to let the projection 3 separate from the main body 2 without causing separation between the connection sheet 34 and the laminated sheet 30. At this time, since an obliquely upward and rightward force Fa acts on the projection 3, as shown in FIG. 12, the bonds due to the embossments 44 in the temporarily fixing region 43 are dissolved from the left side toward the center O2.

In FIG. 12, some of the bonds due to the embossments 44 are dissolved, while the rest remain undissolved. In this state, even when the forces F1, F2 act on the main body 2, their influences on the projection 3 can be reduced to maintain the projection 3 within the intergluteal cleft 61.

If the forces F1, F2 are excessively strong, all or almost all the bonds between the connection sheet 34 and the topsheet 23 due to the embossments 44 are dissolved in the temporarily fixing region 43 between the boundaries X3, X4 to let the projection 3 separate from the main body 2 between the boundaries X3, X4. At this time, since the projection 3 is no more restricted between the boundaries X3, X4, as shown in FIG. 8(B), the apex 3a of the projection 3 subjected to the elastic contractive force of the elastic member 33 tends to move away from the body surface of the main body 2, which increases pressure to push the apex 3a of the projection 3 into the intergluteal cleft 61 and improves contact of the projection 3 with the intergluteal cleft. In addition, even when the main body 2 moves from side to side along with the undergarment 55 during walking, the projection 3 between the boundaries X3, X4 is effectively prevented from slipping off the intergluteal cleft 61.

In both the front firmly fixing region 41 in front of the boundary X3 and the rear firmly fixing region 42 behind the boundary X4, however, the projection 3 and the main body 2 are firmly fixed together. In the projection 3, therefore, the front and rear portions remain fixed on and restricted by the main body 2 while only the intermediate portion between the boundaries X3, X4 is movable independently of the main body 2, which ensures that the intermediate portion will return to its original position along the longitudinal centerline Oy in the upright position shown in FIGS. 11(A) and 11(B).

Now there will be described preferred properties of the components of the sanitary napkin 1 to enable the above described behaviors.

Figure 22:
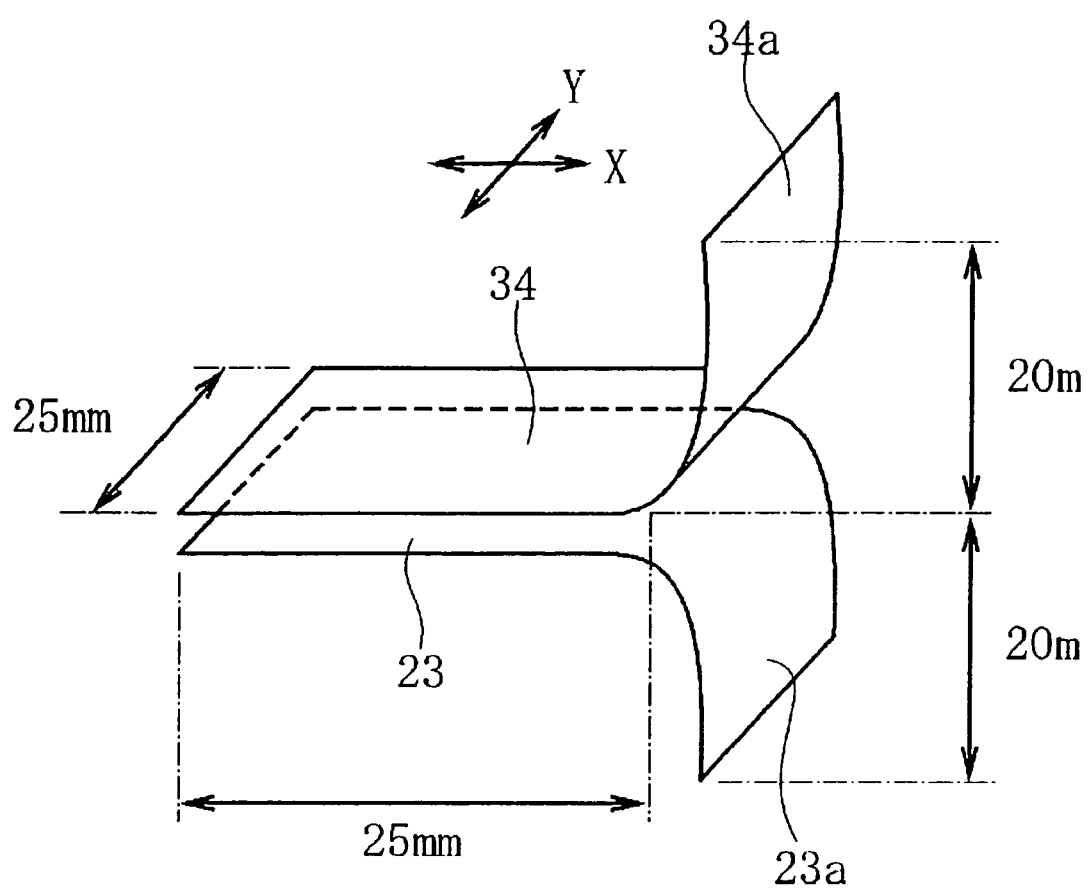
FIG. 22 is an illustration showing a method for measuring bond strength due to temporarily fixing means.

The bond strength between the connection sheet 34 and the topsheet 23 in the temporarily fixing region 43 may be measured in accordance with a method shown in FIG. 22.

The same sheet material as used for the topsheet 23 and the same sheet material as used for the connection sheet 34 are cut into a size having a width of 25 mm and a length of 45 mm. These pieces are separably fixed together under the same conditions as those in the temporarily fixing region 43. At this time, the X-direction of the sample is taken along the width W2 of the temporarily fixing region 43, and the embossments 44 are arranged over the entire length in the Y-direction. In order to prevent tear, reinforcing tapes are adhered to 20 mm tabs 34a, 23a. Measurement is carried out after the sample is left to stand for 30 minutes at a temperature of 20° C. and a relative humidity of 60%. The individual tabs 34a, 23a are held over 10 mm by chucks of an instron tensile tester with an initial chuck distance of 20 mm and then pulled in opposite directions at a rate of 100 mm/min. A maximum load measured during this test is taken as the bond strength. The bond strength is the average of values measured for five samples.

In the temporarily fixing region 43, the bond strength between the connection sheet 34 and the topsheet 23 is preferably in the range of 0.1 to 2.0 N, more preferably in the range of 0.1 to 0.9 N. In this embodiment, for example, the bond strength in the temporarily fixing region 43 is 0.59 N. If it is within the above range, the motion of the undergarment 55 during walking can easily dissolve some or all of the bonds between the connection sheet 34 and the topsheet 23 in the temporarily fixing region 43, as shown in FIGS. 11 and 12.

In the front and rear firmly fixing regions 41, 42, on the other hand, the bond strength between the connection sheet 34 and the topsheet 23 is preferably equal to or greater than 2.5 N as measured in accordance with the method shown in FIG. 22. If it is within the above range, at least one of the sheet materials used for the topsheet 23, the connection sheet 34 and the laminated sheet 30 will be broken by a force to separate the main body 2 and the projection 3 from each other.

Here it is also possible to forcibly separate the projection 3 from the main body 2 with fingers in the temporarily fixing region 43 after the projection 3 is positioned along the intergluteal cleft at the time of wearing the sanitary napkin 1 in the wearer's crotch. If the projection 3 is to be forcibly separated, as set forth above, the bond strength in the temporarily fixing region 43 may be equal to or greater than 1.0 N. The upper limit may be arbitrarily determined as long as the separation of the projection 3 from the main body 2 does not cause serious damage to the components of the sanitary napkin 1.

FIGS. 10(A), 10(B), 10(C) and 10(D) show other embodiments of the temporarily fixing means for separably fixing the connection sheet 34 to the topsheet 23 in the temporarily fixing region 43.

Figure 10A:
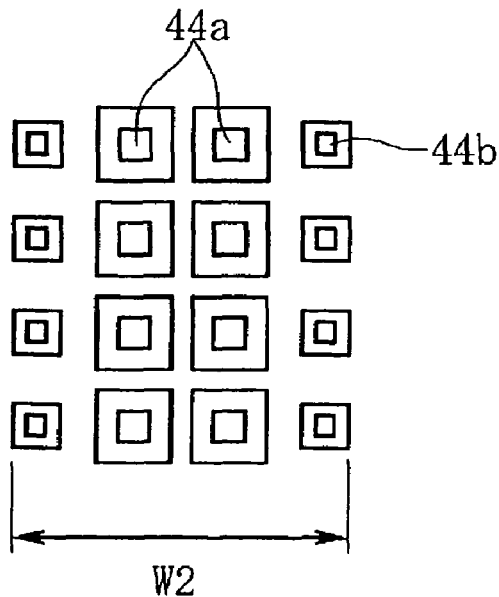
FIGS. 10(A), 10(B), 10(C) and 10(D) show other embodiments of embossments being temporarily fixing means.

The temporarily fixing means shown in FIG. 10(A) is composed of two central rows of the embossments 44a and two outside rows of embossments 44b. Since the embossment 44b has a smaller compression area than the embossment 44a, the bond strength is lower in the embossment 44b than in the embossment 44a.

When the main body 2 and the projection 3 are pulled in generally opposite directions by the motion of the body 60, as shown in FIG. 12, a peel force first acts on one side of the temporarily fixing region 43. Since the embossments 44b located along both sides of the temporarily fixing region 43 have a weak bond strength, the topsheet 23 and the connection sheet 34 can easily be separated from each other to maintain the projection 3 within the intergluteal cleft 61 of the body 60. When a greater force acts thereon, separation of the topsheet 23 and the connection sheet 34 may also occur in the embossments 44a located centrally of the temporarily fixing region 43.

Figure 10B:
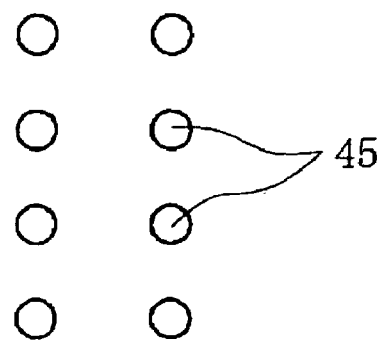
Figure 10C:
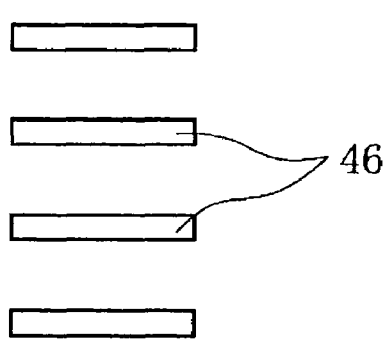
Figure 10D:
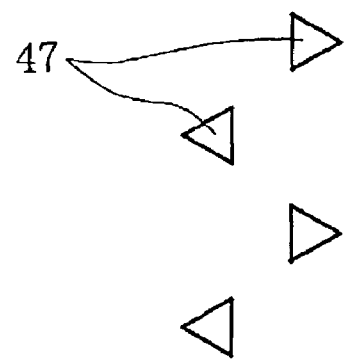

The temporarily fixing means in the temporarily fixing region 43 may be composed of dot-shaped embossments 45 arranged at spaced intervals as shown in FIG. 10(B), laterally extending embossments 46 arranged in a stripe pattern as shown in FIG. 10(C), or small triangular embossments 47 arranged at spaced intervals as shown in FIG. 10(D). These embossments 45, 46, 47 may be formed by pressing the topsheet 23 and the connection sheet 34 at room temperature, as in the first embodiment, or by fusion-bonding (e.g., heat sealing or ultrasonic sealing) the topsheet 23 and the connection sheet 34. In case of heat sealing or ultrasonic sealing, heat-fusible fibers contained in the topsheet 23 and the connection sheet 34 are melted and solidified. In this case, the bond strength in the temporarily fixing region 43 can be set within the above preferred range by appropriately reducing the amount of the heat-fusible fibers contained in the topsheet 23 and the connection sheet 34.

As the temporarily fixing means, alternatively, a pressure-sensitive adhesive layer may be employed to bond the topsheet 23 and the connection sheet 34. In this case, the pressure-sensitive adhesive layer may be applied in the temporarily fixing region 43 in the form of a strip along the longitudinal centerline or in the same pattern as the embossments 45, 46, 47 shown in FIGS. 10(B), 10(C), 10(D). It is also possible to separably fix the topsheet 23 and the connection sheet 34 only at the midpoint between the boundaries X3, X4 through the temporarily fixing means.

Preferably, the raised portion of the projection 3 between the vagina-facing reference line X1 and the rear reference line X2 is capable of recovering after removal of an applied lateral compressive force. For example, the projection 3 shown in FIG. 4 is laterally compressed and flattened to extend vertically from the body surface of the main body 2 at the midpoint between the vagina-facing reference line X1 and the rear reference line X2. When the compressive force is removed, it is preferred that the distance between the side walls of the projection 3 recovers to at least 50% of the original distance, more preferably, at least 60% of the original distance. It is also preferred that the compressive force required to laterally compress and flatten the projection 3 at the midpoint between the vagina-facing reference line X1 and the rear reference line X2 is equal to or less than 20 N/cm$^2$.

If the compressive force required to flatten the raised portion of the projection 3 is within the above range, the projection 3 fitting in the intergluteal cleft 61 can easily be flattened between the buttocks without giving an unpleasant feeling to the intergluteal cleft 61. If the compression recovery ratio is within the above range, the exterior surface of the projection 3 can be kept in contact with the wearer's skin in the intergluteal cleft 61 even if the width of the intergluteal cleft 61 changes during walking.

In the sanitary napkin 1 of the first embodiment, as shown in FIG. 7, the fine irregularities are formed in the exterior sheet 31 of the projection 3 as means for increasing friction. Also, in order to increase friction, the exterior sheet 31 may be made of fibers which can be further crimped by heat treatment. For example, there may be employed a through-air bonded nonwoven fabric formed from the above fibers. The above fibers may be side-by-side bicomponent fibers manufactured by combining two synthetic resin components with different melting points. By heat-treating the nonwoven fabric to further crimp the fibers, fine wrinkles can be created on the surface of the nonwoven fabric. Alternatively, the exterior sheet 31 may be a fiber implanted nonwoven fabric which is prepared by electrostatically implanting a large number of fine fibers in the surface of a nonwoven fabric.

Alternatively, a film or net made of a sticky resin such as urethane resin may be laminated to the exterior surface of the exterior sheet 31. It is also possible to apply a non-slip agent to the exterior surface of the exterior sheet 31. For the non-slip agent, preferably used is a material less irritating to the skin, such as styrene-ethylene-butylene-styrene block copolymer (SEBS) and styrene-ethylene-propylene-styrene block copolymer (SEPS). The non-slip agent may be a pressure-sensitive adhesive which contains 40-60% hydrogenated hydrocarbon resin and 5-15% process oil.

The exterior sheet 31, which shows on the exterior surface of the projection 3, is preferably made of fibers having a fineness of equal to or less than 4 dtex so as to be less irritating to the skin. Preferably, the exterior sheet 31 is a nonwoven fabric having an excellent drapability. In addition to the through-air bonded nonwoven fabric mentioned in the first embodiment, there may be employed a point-bonded nonwoven fabric, a spunlaced nonwoven fabric, a spunbonded nonwoven fabric, a resin film with a large number of apertures for passage of liquid, and a composite of the resin film and the nonwoven fabric. At least one of the exterior sheet 31 and the interior sheet 32 may be capable of absorbing liquid. For example, there may be employed a spunlaced nonwoven fabric of hydrophilic fibers, an air-laid nonwoven fabric in which pulp and optionally synthetic resin fibers are bonded through a binder, and a sheet pulp formed by compressing pulp. The air-laid nonwoven fabric and the sheet pulp are preferably embossed to improve strength, thereby preventing breakage in the sheet upon separation of the projection 3 from the main body 2.

In the first embodiment, although only one string-like elastic member 33 is provided in the apex 3a of the projection 3, as shown in FIGS. 4 and 5, it is also possible to provide a plurality of the elastic members. These elastic members may be disposed at portions other than the apex 3a. On the other hand, the string-like elastic member 33 may be omitted, if desired. In this case, an elastically stretchable nonwoven fabric may be employed for at least one of the exterior sheet 31 and the interior sheet 32 or the projection 3 may be formed of a laminate of a film-like or net-like elastic member and a nonwoven fabric.

In the first embodiment, although the projection 3 is raised from the body surface of the main body 2 by the elastic contractive force of the elastic member 33, the projection of the present invention should not be construed as limited thereto. For example, the projection 3 may be formed of a 40-100 g/m² bulky through-air bonded nonwoven fabric comprising fibers having a fineness of equal to or greater than 4 dtex. This through-air bonded nonwoven fabric may be folded in two or more. Alternatively, the projection 3 may be formed of a point-bonded, spunlaced or spunbonded nonwoven fabric, which is embossed to have irregularities and increase the bulk or folded or laminated. The projection 3 may also be formed by laminating an air-laid nonwoven fabric and a sheet pulp.

Now there will be described sanitary napkins according to other embodiments of the present invention.

In the following embodiments, the detailed description of the portions having the same construction as those of the first embodiment will be omitted by designating them by the common reference numerals.

Figure 13:
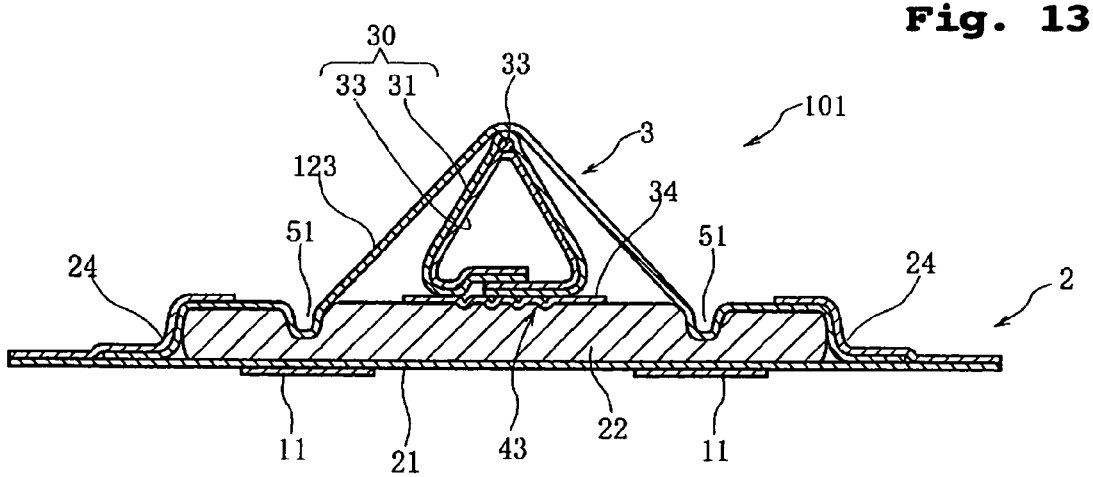
FIG. 13 is a sectional view of a sanitary napkin according to a second embodiment of the present invention.

FIG. 13 is a sectional view taken in the temporarily fixing region 43 as in FIG. 4, showing a sanitary napkin 101 according to a second embodiment of the present invention.

The sanitary napkin 101 differs from the sanitary napkin 1 of the first embodiment in that the sanitary napkin 101 has a topsheet 123 which is liquid-permeable and disposed to cover not only the body surface of the liquid-absorbent layer 22 of the main body 2 but also the tubular laminated sheet 30. In the temporarily fixing region 43, the connection sheet 34 is separably fixed to the body surface of the liquid-absorbent layer 22; in the front and rear firmly fixing regions 41, 42, the connection sheet 34 is firmly fixed to the body surface of the liquid-absorbent layer 22. Here it is preferred that the liquid-absorbent layer 22 is formed by wrapping pulp in a hydrophilic paper or nonwoven fabric and the connection sheet 34 is separably or firmly fixed to the hydrophilic paper or nonwoven fabric. In the sanitary napkin 101, the topsheet 123 forms not only a part of the main body 2 but also a part of the projection 3.

When the main body 2 and the projection 3 are pulled in generally opposite directions, the tubular laminated sheet 30 and the connection sheet 34, which are separated from the main body 2 in the temporarily fixing region 43, move from side to side beneath the topsheet 123, which prevents the excessive rise of the tubular laminated sheet 30 and the connection sheet 34 from the body surface of the main body 2.

Figure 14:
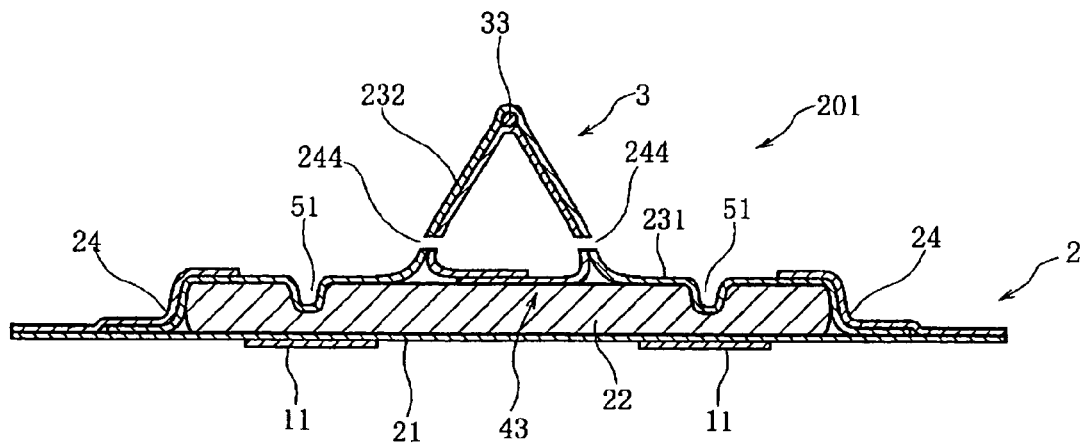
FIG. 14 is a sectional view of a sanitary napkin according to a third embodiment of the present invention.

FIG. 14 is a sectional view taken in the temporarily fixing region 43 as in FIGS. 4 and 13, showing a sanitary napkin 201 according to a third embodiment of the present invention.

The projection 3 is formed of a liquid-permeable interior sheet 232 and a liquid-permeable exterior sheet 231 covering the interior sheet 232. The exterior sheet 231 is bonded at its central portion to the interior sheet 232 through a hot-melt type adhesive and at its side portions to the body surface of the liquid-absorbent layer 22 of the main body 2.

In the temporarily fixing region 43, the interior sheet 232 and the exterior sheet 231 have cuts 244 at lower parts of the side walls of the projection 3. The cuts 244 are arranged at spaced intervals in the longitudinal direction in the form of perforation. In the front and rear firmly fixing regions 41, 42, on the other hand, the projection 3 does not have the cuts 244. In the third embodiment, the cuts 244 function as the temporarily fixing means.

In the sanitary napkin 201, when the main body 2 and the projection 3 are pulled in generally opposite directions, the interior sheet 232 and the exterior sheet 231 can be torn along the cuts (or perforation) 244 to enable the projection 3 to move independently of the main body 2 in the temporarily fixing region 43.

Figure 15:
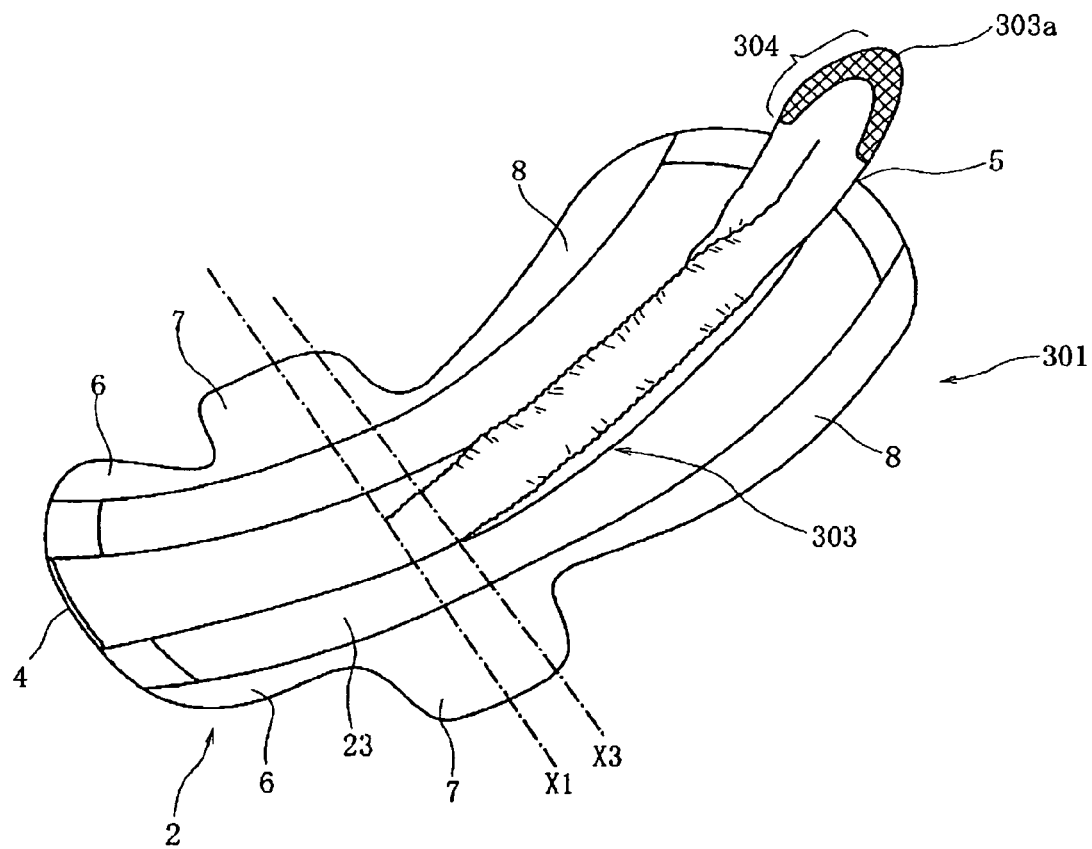
FIG. 15 is a sectional view of a sanitary napkin according to a fourth embodiment of the present invention in a state where no external force is exerted thereon.
Figure 16:
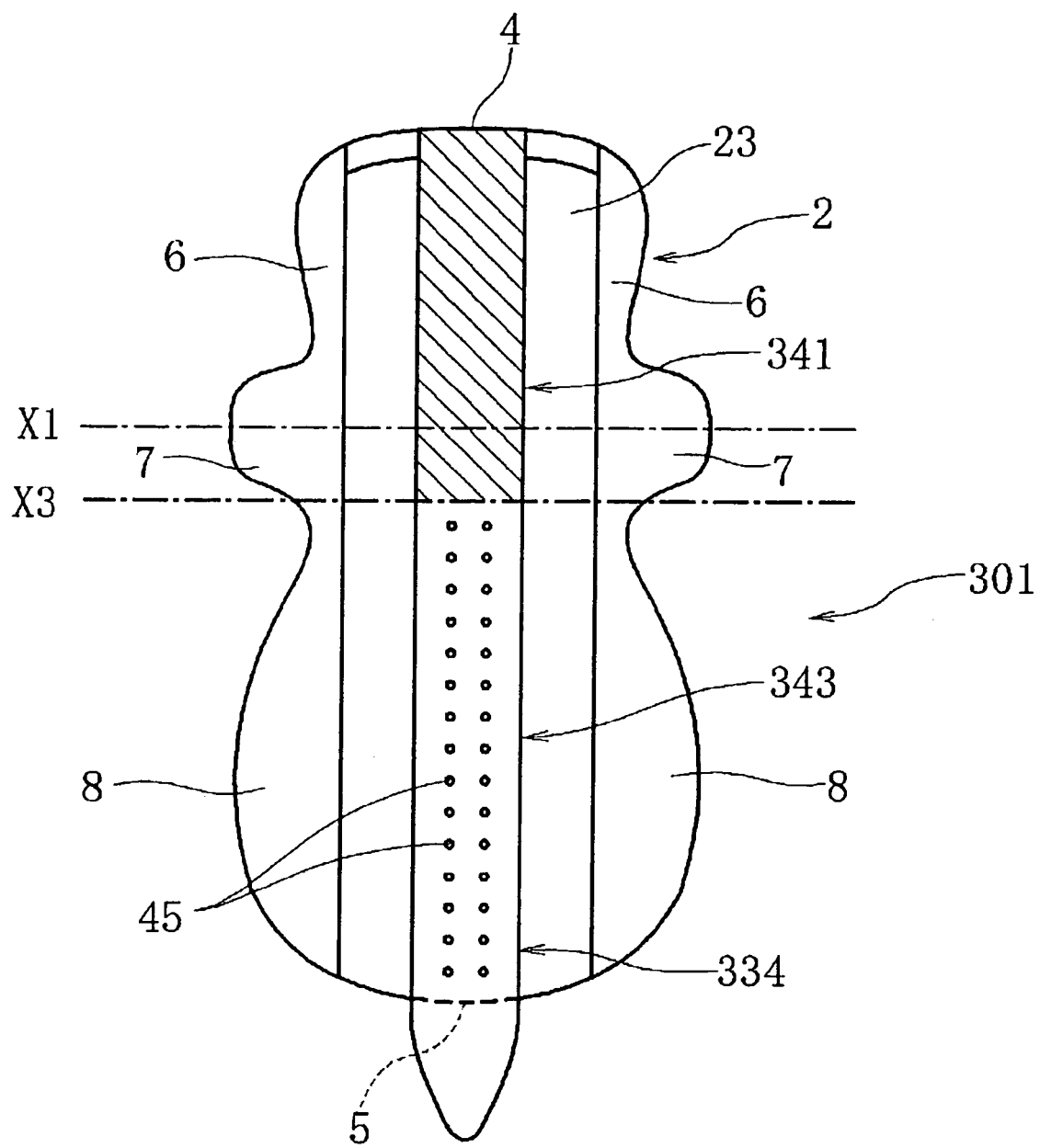
FIG. 16 is a plan view of the sanitary napkin of FIG. 15 in which a main body is flattened.

FIG. 15 is a perspective view of a sanitary napkin 301 according to a fourth embodiment of the present invention in a state where no external force is exerted thereon, and FIG. 16 is a plan view in which the main body 2 and a connection sheet 334 are flattened.

In the sanitary napkin 301, the main body 2 has the same construction as that in the sanitary napkin 1 of the first embodiment. A projection 303 is formed of the tubular laminated sheet 30, the elastic member 33 and the connection sheet 334 like the projection 3 in the sanitary napkin 1 of the first embodiment. Here it is possible not to provide the elastic member 33 in the projection 303.

As shown in FIG. 16, the sanitary napkin 301 has a firmly fixing region 341 between the boundary X3 and the front edge 4. In the firmly fixing region 341, the connection sheet 334 and the topsheet 23 of the main body 2 are firmly fixed together. On the other hand, the sanitary napkin 301 has a temporarily fixing region 343 between the boundary X3 and the rear edge 5. In the temporarily fixing region 343, the connection sheet 334 and the topsheet 23 of the main body 2 are separably fixed together at embossments 45 which are formed by heat sealing at spaced intervals as shown in FIG. 10(B).

The projection 303 extends rearward beyond the rear edge 5 to have a tab 304 which are not fixed to the main body 2. In the tab 304 behind the rear edge 5, the tubular laminated sheet 30 and the connection sheet 334 are flattened and heat sealed to have a seal 303a.

Figure 17A:
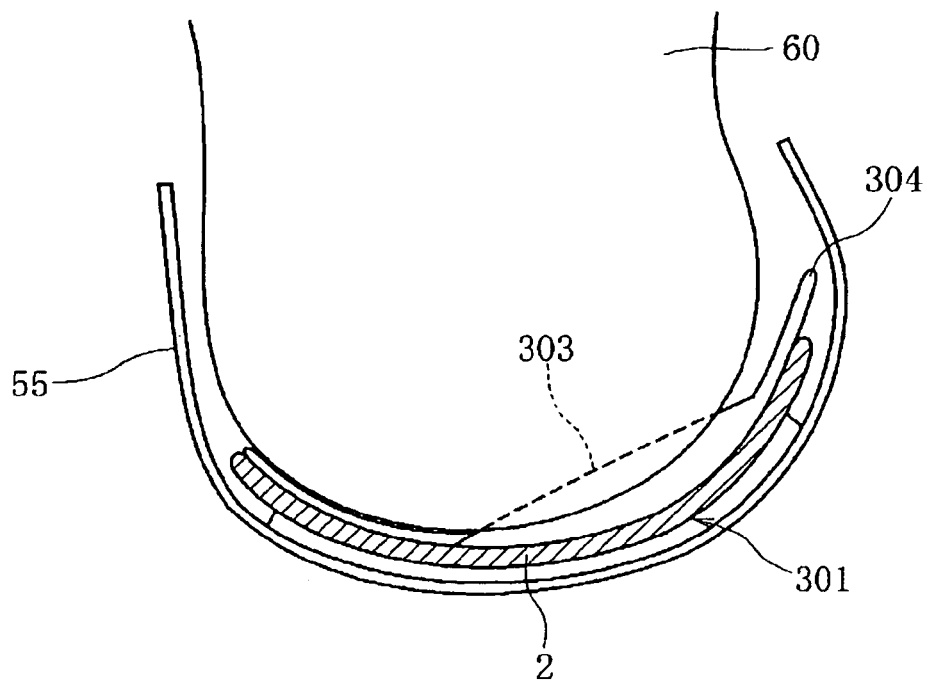
FIGS. 17(A) and 17(B) are illustrations showing how to wear the sanitary napkin of FIG. 15.
Figure 17B:
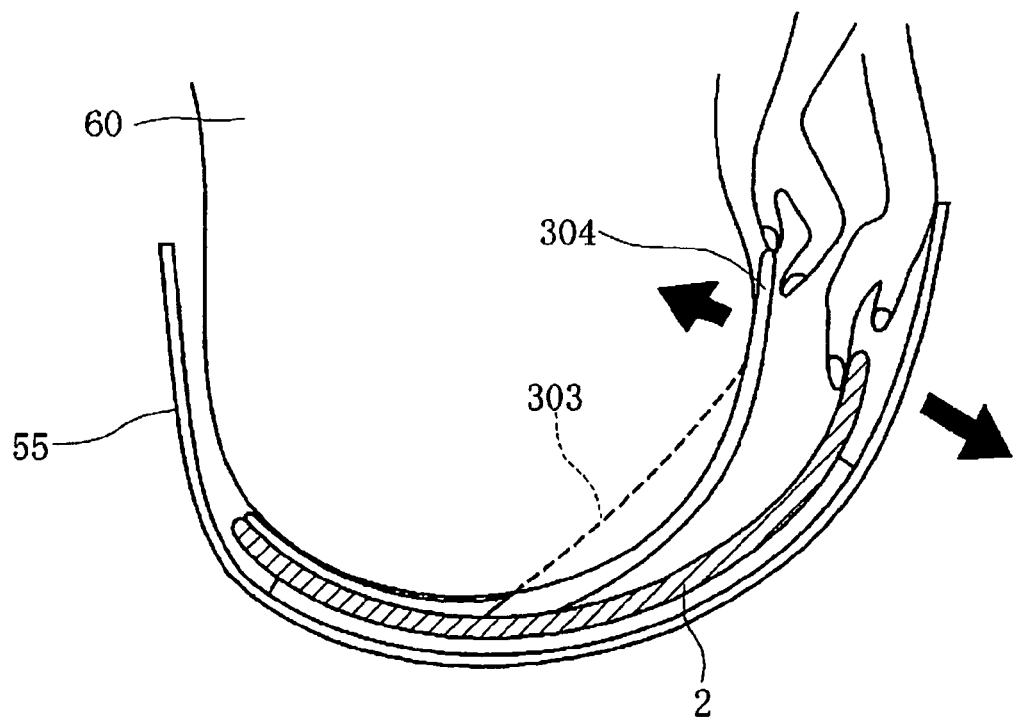

FIGS. 17(A) and 17(B) are illustrations showing how to wear the sanitary napkin 301.

As shown in FIGS. 17(A), the main body 2 of the sanitary napkin 301 is secured to the inner side of the crotch part of the undergarment 55, and the sanitary napkin 301 is applied to the crotch of the body 60 along with the undergarment 55. After the projection 303 is positioned along and fitted in the intergluteal cleft, the tab 304 is pulled away from the undergarment 55 by hands, as shown in FIG. 17(B), thereby dissolving the bonds between the connection sheet 334 and the main body 2 in the temporarily fixing region 343 to have the projection 303 unfixed behind the boundary X3.

Then, the projection 303 can be maintained within the intergluteal cleft even if the main body 2 moves along with the undergarment 55.

Figure 18:
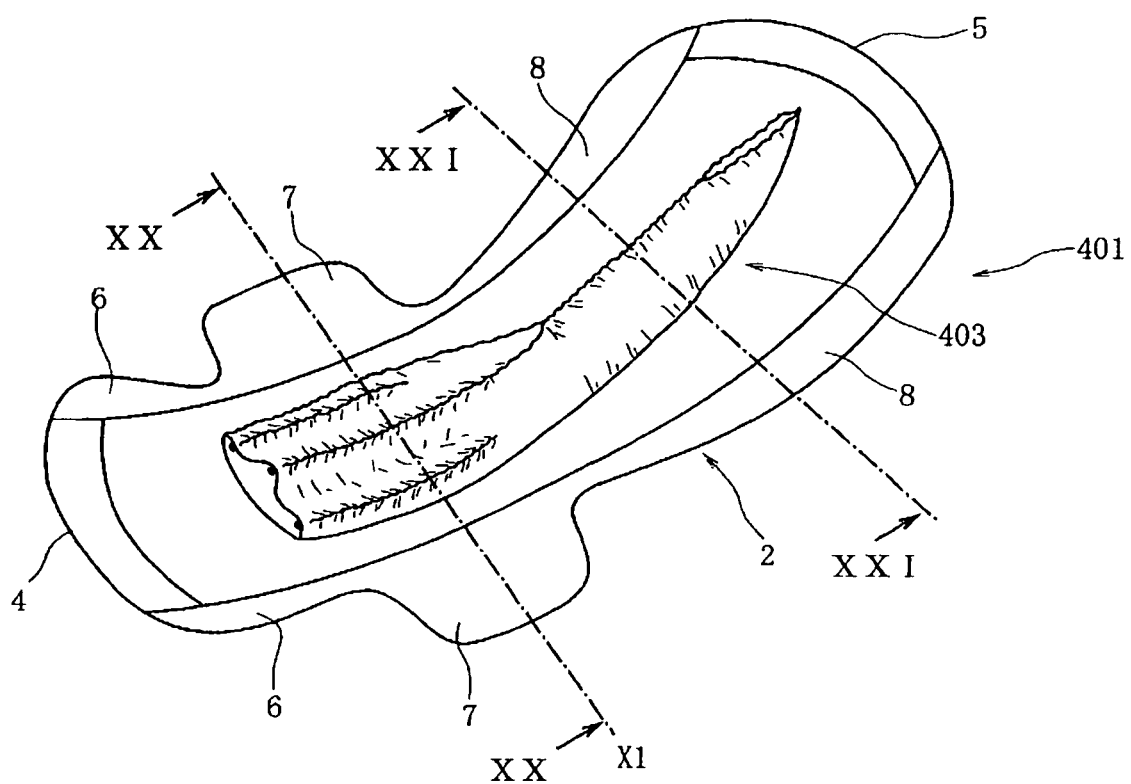
FIG. 18 is a perspective view of a sanitary napkin according to a fifth embodiment of the present invention in a state where no external force is exerted thereon.
Figure 19:
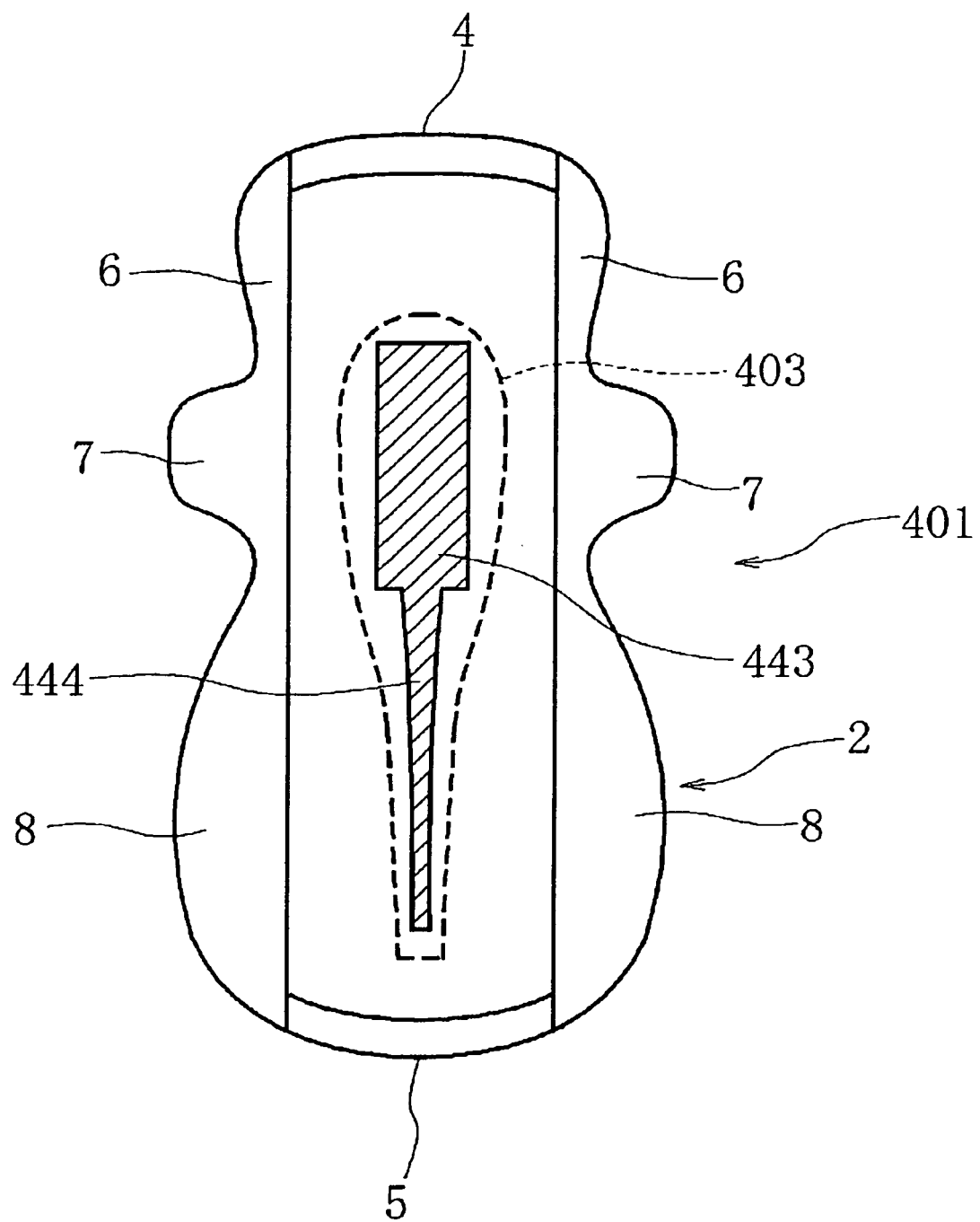
FIG. 19 is a plan view of the sanitary napkin of FIG. 18 in which a main body is flattened.

FIG. 18 is a perspective view of a sanitary napkin 410 according to a fifth embodiment of the present invention in a state where no external force is exerted thereon, and FIG. 19 is a plan view in which the main body 2 is flattened. FIG. 20 is a sectional view taken along line XX-XX (which coincides with the vagina-facing reference line X1) of FIG. 18, and FIG. 21 is a sectional view taken along line XXI-XXI (which extends across the intergluteal cleft facing portion) of FIG. 18.

In the sanitary napkin 401, a projection 403 is separably fixed to the body surface of the main body 2 as a whole. In a temporarily fixing region 443, as shown in FIG. 19, the projection 403 and the body surface of the main body 2 are separably fixed together through a hot-melt type pressure-sensitive adhesive layer 444.

As shown in FIGS. 20 and 21, the projection 403 has an exterior sheet 431 and an interior sheet 432. The exterior sheet 431 may be a spunlaced nonwoven fabric having an excellent water retentivity. The interior sheet 432 may be a nonwoven fabric formed of thick fibers and having a large basis weight so as to maintain three dimensional shape. This nonwoven fabric may be, for example, a 60 g/m² through-air bonded nonwoven fabric of 5.5 dtex sheath/core bicomponent fibers of which the core is polypropylene and the sheath is polyethylene. The interior sheet 432 is formed into a tube with their opposite edges bonded together through a hot-melt type adhesive 436. The exterior sheet 431 is also formed into a tube with their opposite edges bonded together through a hot-melt type adhesive 437. The exterior sheet 431 is separably fixed to the body surface of the main body 2 through the pressure-sensitive adhesive layer 444.

At a vaginal opening facing portion of the projection 403, as shown in FIG. 20, the opposite inner surfaces of the interior sheet 432 are bonded to each other at three points through hot-melt type adhesives 438, 439 to maintain the projection 403 in a generally flattened state. At a intergluteal cleft facing portion of the projection 403, as shown in FIG. 21, the opposite inner surfaces of the interior sheet 432 are bonded to each other along the longitudinal centerline through the hot-melt type adhesive 438 to maintain the projection 403 in a three dimensional shape having a generally triangular section.

In the sanitary napkin 401, the interior sheet 432 of the projection 403 is sufficiently stiff to maintain three dimensional shape, ensuring that the rear portion of the projection 403 will fit in the intergluteal cleft. When the main body 2 and the projection 403 are pulled in generally opposite directions during wear, the temporary fixation due to the pressure-sensitive adhesive layer 444 will be dissolved to permit partial or overall separation of the projection 403 from the main body 2.

In the foregoing embodiments, the intergluteal cleft facing portion of the projection is separably fixed to the main body 2 in the temporarily fixing region. In the present invention, however, it is also possible to separably fix another portion of the projection, such as the vaginal opening facing portion or the perineum or anus facing portion, to the main body through the temporarily fixing means.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising:
   a main body having a liquid-absorbent layer for absorbing and retaining liquid; and
   a projection disposed on a body surface of the main body, the projection being divided into front and rear portions,
   wherein the rear portion of the projection is separably fixed to the body surface of the main body through a temporarily fixing means, such that the rear portion of the projection can be easily separated from the main body without causing damage to components of the projection and main body, the temporarily fixing means being provided on a garment surface of the projection,
   wherein the temporarily fixing means provides a bond strength such that the projection and the main body can be separated from each other without changing in shape,
   wherein the front portion of the projection is firmly fixed to the body surface of the main body through a firmly fixing means which provides a higher bond strength than the temporarily fixing means,
   wherein the bond strength provided by the temporarily fixing means is 0.1-2.0 Newtons, and
   wherein the bond strength provided by the firmly fixing means is greater than or equal to 2.5 Newtons.

2. The sanitary napkin of claim 1, wherein the projection has front and rear portions and an intermediate portion located between the front and rear portions, the front and rear portions being firmly fixed to the body surface of the main body through the firmly fixing means, the intermediate portion being separably fixed to the body surface of the main body through the temporarily fixing means.

3. The sanitary napkin of claim 2, wherein the projection is configured to face the intergluteal cleft of a wearer at the intermediate portion.

4. The sanitary napkin of claim 1, wherein the rear portion has a tab at a rear end thereof.

5. The sanitary napkin of claim 4, wherein the tab is not fixed to the main body.

6. The sanitary napkin of claim 1, wherein the projection includes a longitudinally extending connection sheet and an upper structure, the connection sheet being fixed to the body surface of the main body through the temporarily fixing means and firmly fixing means, the upper structure being firmly fixed to a body surface of the connection sheet.

7. The sanitary napkin of claim 1, wherein the whole projection is separably fixed to the body surface of the main body through the temporarily fixing means.

8. The sanitary napkin of claim 1, wherein the temporarily fixing means comprises embossments formed by partially pressing a component of the projection against the body surface of the main body.

9. The sanitary napkin of claim 1, wherein the temporarily fixing means is provided by partially fusion-bonding a component of the projection to the body surface of the main body.

10. The sanitary napkin of claim 1, wherein the temporarily fixing means is an adhesive layer through which the projection is separably bonded to the body surface of the main body.

11. The sanitary napkin of claim 1, wherein the temporarily fixing means is provided by perforating a component of the projection at intervals.

12. The sanitary napkin of claim 4, wherein temporarily fixing means is operable to be released by pulling on the tab, such that upon release the projection and the main body are separated from each other without substantial damage.

13. The sanitary napkin of claim 1, wherein the firmly fixing means occupies a firmly fixing region extending from a front edge of the main body to a boundary transversely positioned across a longitudinal centerline of the main body, and the temporarily fixing means occupies a temporarily fixing region extending from the boundary to a rear edge of the main body.

14. The sanitary napkin of claim 1, wherein the projection includes:
   a tubular laminated sheet;
   an elastic member extending within an upper portion of the tubular laminated sheet; and
   a connection sheet positioned between the tubular laminated sheet and the main body.

15. The sanitary napkin of claim 1, further comprising a tab of the projection extending beyond the rear edge of the main body, the tab being formed by flattening and heat sealing a rearmost portion of the tubular laminated sheet to the connection sheet.

16. The sanitary napkin of claim 13, wherein the temporarily fixing means comprises dot-shaped embossments formed by heat sealing at spaced intervals within the temporarily fixing region.

17. The sanitary napkin of claim 13, wherein the temporarily fixing means comprises an adhesive applied in a dot-shaped pattern at spaced intervals within the temporarily fixing region.

* * * * *